United States Patent [19]
John et al.

[11] Patent Number: 5,994,398
[45] Date of Patent: Nov. 30, 1999

[54] ARYLSULFONAMIDES AS PHOSPHOLIPASE A₂ INHIBITORS

[75] Inventors: Varghese John, San Francisco; Russell E. Rydel, Belmont; Eugene D. Thorsett, Moss Beach, all of Calif.

[73] Assignee: Elan Pharmaceuticals, Inc., South San Francisco, Calif.

[21] Appl. No.: 08/766,554

[22] Filed: Dec. 11, 1996

[51] Int. Cl.⁶ .......................... A01N 47/10; A01N 47/28; C07C 333/00; C07C 273/00
[52] U.S. Cl. .......................... 514/485; 514/597; 514/603; 558/241; 560/12; 564/49; 564/86
[58] Field of Search .......................... 560/12; 558/241; 564/49, 86

[56] References Cited

U.S. PATENT DOCUMENTS

| | | | |
|---|---|---|---|
| 4,666,829 | 5/1987 | Glenner et al. | 435/6 |
| 5,137,873 | 8/1992 | Yanker | 514/15 |
| 5,192,753 | 3/1993 | McGeer et al. | 514/159 |
| 5,276,059 | 1/1994 | Caughey et al. | 514/647 |
| 5,281,626 | 1/1994 | Oinuma et al. | 514/603 |
| 5,322,776 | 6/1994 | Knopf et al. | 435/69.1 |
| 5,328,842 | 7/1994 | Chiou et al. | 435/240.2 |
| 5,354,677 | 10/1994 | Knopf et al. | 435/198 |
| 5,453,443 | 9/1995 | Perrier et al. | 514/570 |
| 5,466,595 | 11/1995 | Jones et al. | 435/240.2 |
| 5,478,857 | 12/1995 | Clemens et al. | 514/381 |
| 5,530,118 | 6/1996 | Oinuma et al. | 540/364 |
| 5,554,511 | 9/1996 | Jones et al. | 435/69.1 |
| 5,707,821 | 1/1998 | Rydel et al. | 435/18 |
| 5,866,318 | 2/1999 | Rydel et al. | 435/4 |

FOREIGN PATENT DOCUMENTS

| | | | |
|---|---|---|---|
| 0 468 054 A1 | 1/1992 | European Pat. Off. | C07C 311/46 |
| 0 611 003 A1 | 8/1994 | European Pat. Off. | C07C 311/21 |
| WO 96/40982 | 12/1996 | WIPO | C12Q 1/34 |

OTHER PUBLICATIONS

Lalizari, et al., "Synthesis of new urethans. *p*Cyclohexylsufamoyl and *p*Piperidinosulfonylcarbanilic acid esters," *J. Med. Chem.*, 14(10):1017–1021 (1971).

Wadsworth, et al., "Synthetic applications of phosphorylstabilized anions," *Org. React.*, 25:73–253 (1977).

Glenner, et al., "Alzheimer's disease: Initial report of the purification and characterization of a novel cerebrovascular amyloid protein," *Biochem. Biophys. Res. Commun.*, 120(3):885–890 (May 16, 1984).

Martin, et al., "Inhibitors of protein synthesis and RNA synthesis prevent neuronal death caused by nerve growth factor deprivation," *J. Cell Biol.*, 106:829–844 (1988).

Tanzi, R.E., "Protease inhibitor domain encoded by an amyloid protein precursor mRNA associated with Alzeimer's disease," *Nature*, 331:528–530 (1988).

Ponte, et al., "A new A4 amyloid mRNA contains a domain homologous to serine proteinase inhibitors," *Nature*, 331:525–527 (1988).

Kitaguchi, et al., "Novel precursor of Alzheimer's disease amyloid protein shows protease inhibitory activity," *Nature*, 331: 530–532 (1988).

Neve, et al., "The Alzheimer amyloid precursor–related transcript lacking the β/A4 sequence is specifically increased in Alzheimer's disease brain," *Neuron*, 5:329–338 (Sep. 1990).

Yankner, et al., "Neurotrophic and neurotoxic effects of amyloid β protein: reversal by tachykinin neuropeptides," *Science*, 250:279–282 (Oct. 12, 1990).

Kang, et al., "Differential splicing of Alzheimer's disease amyloid A4 precursor RNA in rat tissues: preA4₆₉₅ mRNA is predominantly produced in rat and human brain," *Biochem. Biophys. Res. Commun.*, 166(3):1192–1200 (Feb. 14, 1990).

Johnson, et al., "Relation of neuronal APP–751/APP–695 mRNA ratio and neuritic plaque density in Alzheimer's disease," *Science*, 248:854–857 (May 18, 1990).

Clark, et al., "A novel arachidonic acid–selective cytosolic $PLA_2$ contains a $Ca^{2+}$–dependent translocation domain with homology to PKC and GAP," *Cell*, 65:1043–1051 (Jun. 14, 1991).

Oinuma, et al., "Synthesis and biological evaluation of substituted benzenesulfonamides as novel potent membrane–bound phospholipase $A_2$ inhibitors," *J. Med. Chem.*, 34(7):2260–2267 (1991).

Sharp, et al., "Molecular cloning and expression of human $Ca^{2+}$–sensitive cytosolic phospholipase $A_2$," *J. Biol. Chem.*, 266(23):14850–14853 (1991).

Kowall, et al., "An in vivo model for the neurodegenerative effects of β amyloid and protection by substance P," *Proc. Natl. Acad. Sci.* (USA)m 88L7247–7251 (Aug. 1991).

Yoshioka, et al., "The $^{717}$Val→Ile substitution in amyloid precursor protein is associated with familial Alzheimer's disease regardless of ethnic groups," *BIochem. Biophys. Res. Commun.*, 178(3):1141–1146(Aug. 15, 1991).

Reynolds, et al., "Assay strategies and methods for phospholipases," *Methods in Enzymology*, 197:3–23 (1991).

(List continued on next page.)

*Primary Examiner*—John M. Ford
*Assistant Examiner*—Bruck Kifle
*Attorney, Agent, or Firm*—Townsend & Townsend & Crew

[57] ABSTRACT

Arylsulfonamides which have the general structure:

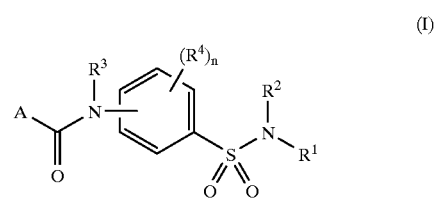

(I)

with the symbols $R^1$, $R^2$, $R^3$, $R^4$, A and n representing the groups and integers provided in the detailed description are provided herein. These compounds have activity as inhibitors of phospholipase A2, inhibitors of cytokine release and as inhibitors of neurodegeneration.

40 Claims, 2 Drawing Sheets

OTHER PUBLICATIONS

Joel N. Buxbaum, "197. The amyloid diseases," 19th Edition: *Cecil Textbook of Medicine*, 1:1141–1145, W.B. Saunders, Philadelphia, PA (1992).

Hardy, et al., "Alzheimer's disease: The amyloid cascade hypothesis," *Science*, 256:184–185 (Apr. 10, 1992).

Seubert, et al., "Isolation and quantifiation of soluble ALzheimer's β–peptide from biological fluids," *Nature*, 359:325–327(Sep. 24, 1992).

Lin, et al., "Cytosolic phospholipase $A_2$ is coupled to hormonally regulated release of arachidonic acid," *Proc. Natl. Acad. Sci.* (USA), 89:6147–6151 (Jul. 1992).

Haass, et al., "Anyloid β–peptide is produced by cultured cells during normal metabolism," *Nature*, 359:322–325 (Sep. 24, 1992).

Mattson, et al., "β–Amyloid peptides destabilize calcium homeostasis and render human cortical neurons vulnerable to excitotoxicity," *J. Neurosci.*, 12(2):376–389 (Feb. 1992).

Qiu, et al., "Regulation of phospholipase $A_2$ activation by phosphorylation in mouse peritoneal macrophages," *J. Biol. Chem.*, 268(32):24506–24513 (1993).

Kramer, et al., "Thrombin–induced phosphorylation and activation of $Ca^{2+}$–sensitive cytosolic phospholipase $A_2$ in human platelets," *J. Biol. CHem.*, 268(35)26796–26804 (Dec. 15, 1993).

Brewer, et al., "Optimized survival of hippocampal neurons in B27–supplemented neurobasal™, a new serum–free medium combination," *J. Neurosci. Res.*, 35(5):567–576 (1993).

Street, et al., "Slow–and tight–binding inhibitors of the 85–kDa human phospholipase $A_2$," *Biochemistry*, 32:5935–5940 (1993).

Verity, M.A., "Mechanisms of phospholipase $A_2$ activation and neuronal injury," *Ann. N.Y. Acad. Sci.*, 679:110 (1993).

Lin, et al., "cPLA$_2$ is phosphorylated and activated by MAP kinase," *Cell*, 72:269–278 (Jan. 29, 1993).

Kramer, "Structure, function and regulation of mammalian phospholipases $A_2$," *Advances in Second Messenger and Phosphorprotein Research*, 28:81–89 (1993).

Pike, et al., "Neurodegeneration induced by β–amyloid peptides in vitro: The role of peptide assembly state," *J. Neurosci.*, 13(4):1676–1687 (Apr. 1993).

Glaser, et al., "Phospholipase $A_2$ enzymes: regulation and inhibition," *TiPS*, 14:92 (Mar. 1993).

Mattson, et al., "β–Amyloid precursor protein metabolities and loss of neuronal $Ca^{2+}$ homeostasis in Alzheimer's disease," *Trends in Neuroscience*, 16(10):409 (Oct. 1993).

Agarwal, et al., "Phospholipase activation triggers apoptosis in photosensitized mouse lymphoma cells," *Cancer Res.*, 53:5897–5902 (Dec. 15, 1993).

Dumuis, et al., "Stimulation by glutamate receptors of arachidonic acid release depends on the $Na^+/Ca^{2+}$ exchanger in neuronal cells," *Mol. Pharmacol.*, 43:976–981 (Mar. 29, 1993).

Roshak, et al., "Suppression of monocyte 85–kDa phospholipase $A_2$ by antisense and efects on endotoxin–induced prostaglandin biosynthesis," *J. Biol. Chem.*, 269(42):25999–26005 (Oct. 21, 1994).

Reyolds, et al., "1–Hexadecyl–2–arachidonoylthio–2–deoxy–sn–glycero–3–phosphorylcholine as a substrate for the microtiterplate assay of human cytosolic phospholipase $A_2$," *Anal. Biochem.*, 217:25–32 (1994).

Currie, et al., "Phosphorylation and activation of $Ca^{2+}$–sensitive cytosolic phospholipase $A_2$ in MCII mast cells mediated by high–affinity $F_c$ receptor for IgE," *Biochem. J.*, 304:923–928 (1994).

Dennis, E.A., "DIversity of group types, regulation, and function of phospholipase $A_2$," *J. Biol. Chem.*, 269(18):13057–13060 (May 6, 1994).

Bartoli, et al., "Tight bonding inhibitors of 85–kDa phospholipase $A_2$ but not 14–kDa phospholipase $A_2$ inhibit release of free arachidonate in thrombin–stimulated human platelets," *J. Biol. Chem.*, 269(22):15625–15630 (May 6, 1994).

Lorenzo, et al., "β–Amyloid neurotoxicity requres fibril formation and is inhibited by Congo red," *Proc. Natl. Acad. Sci.* (USA), 91:12243–12247 (Dec. 1994).

Schubert, et al., "Amyloid peptides are toxic via a common oxidative mechanism," *Proc. Natl. Acad. Sci.* (USA), 92:1989–1993 (Mar. 1995).

Petit, et al., "Isolation and characterization of a cytosolic phospholipase $A_2$ from bovine adrenal medulla," *J. Neurochem.*, 64(1)139–146 (1995).

Meda, et al., "Activation of microglial cells by β–amyloid protein and interferon–γ," *Nature*, 374:647–650 (1995).

Ackermann, et al., "Inhibition of macrophage $Ca^{2+}$–independent phospholipase $A_2$ by bromoenol lactone and trifluoromethyl ketones," *J. Biol. CHem.*, 270(1):445–450 (1995).

Farooqui, et al., "Plasmalogens, phospholipases $A_2$ and signal transduction," *Brain research Reviews*, 21:152–161 (1995).

Abdullah, et al., "Human cytosolic phospholipase $A_2$ expressed in insect cells is extensively phosphorylated on Ser–505," *Biochemics et biophysica Acta*, 1244:157–164 (1995).

Abdullah, et al., "Synthesis and preparation of an affinity chromatography column for the purification of cytosolic phospholipase $A_2$," *Bioorganic & Medicinal Chemistry Letters*, 5(5):519–522 (1995).

Abdullah, et al., "Purification of baculovirus–overexpressed cytosolic phospholipase $A_2$ using a single–step affinity column chromatography," *Protein Expression and Purification*, 6:291–297 (1995).

Lorton, et al., "β–amyloid induces increased release of interleukin–1β from lipopolysaccharide–activated human monocytes," *J. Neuroimmunology*, 67(1996).

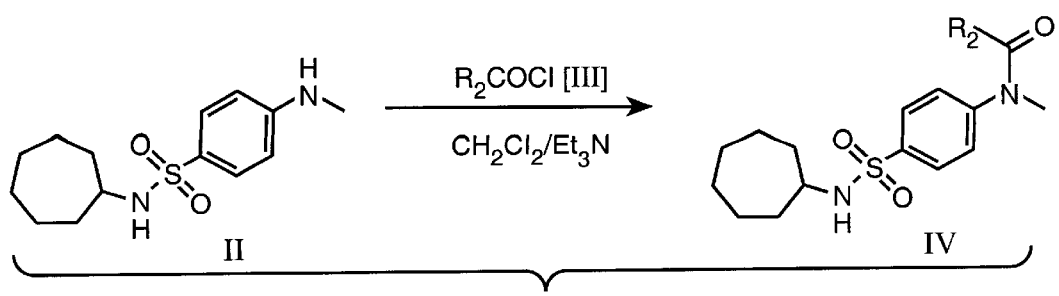
FIG._1A
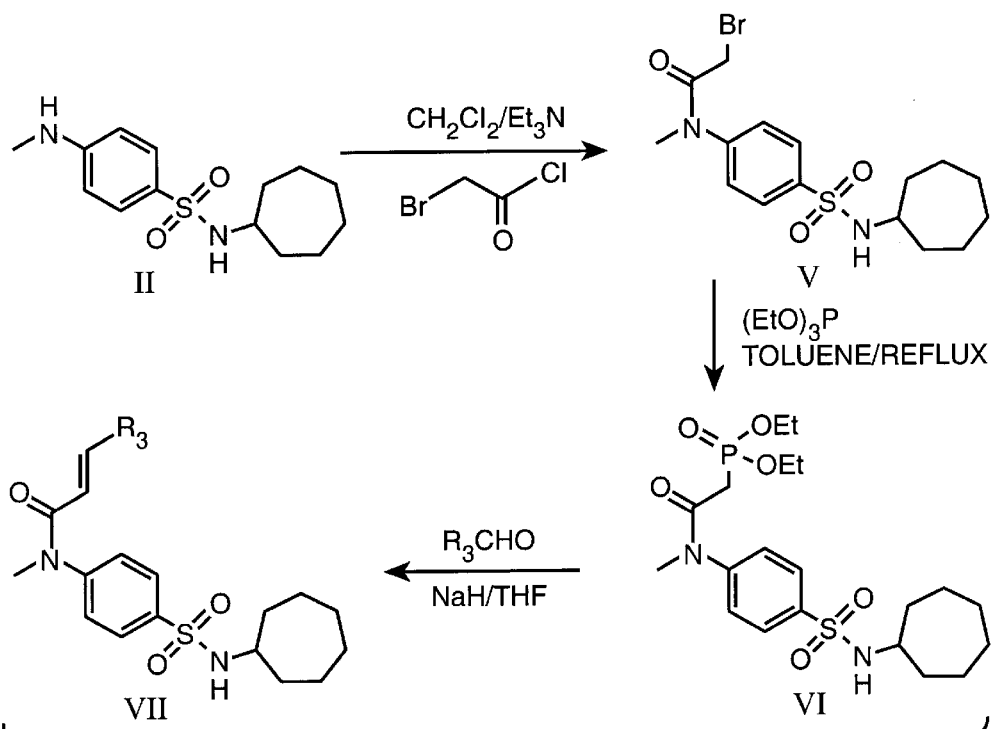
FIG._1B
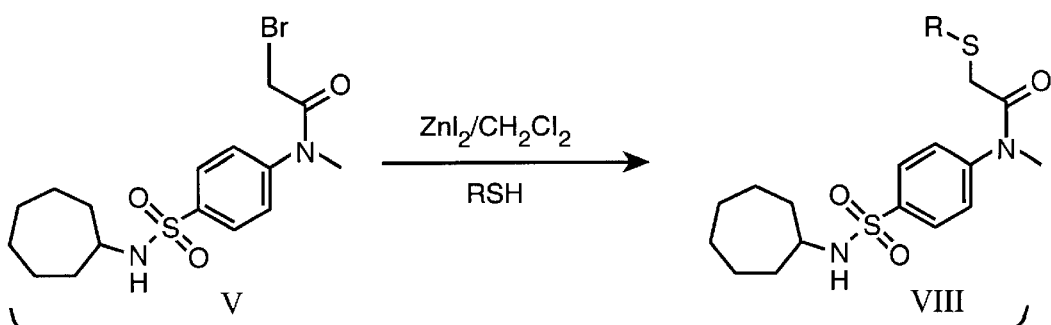
FIG._1C

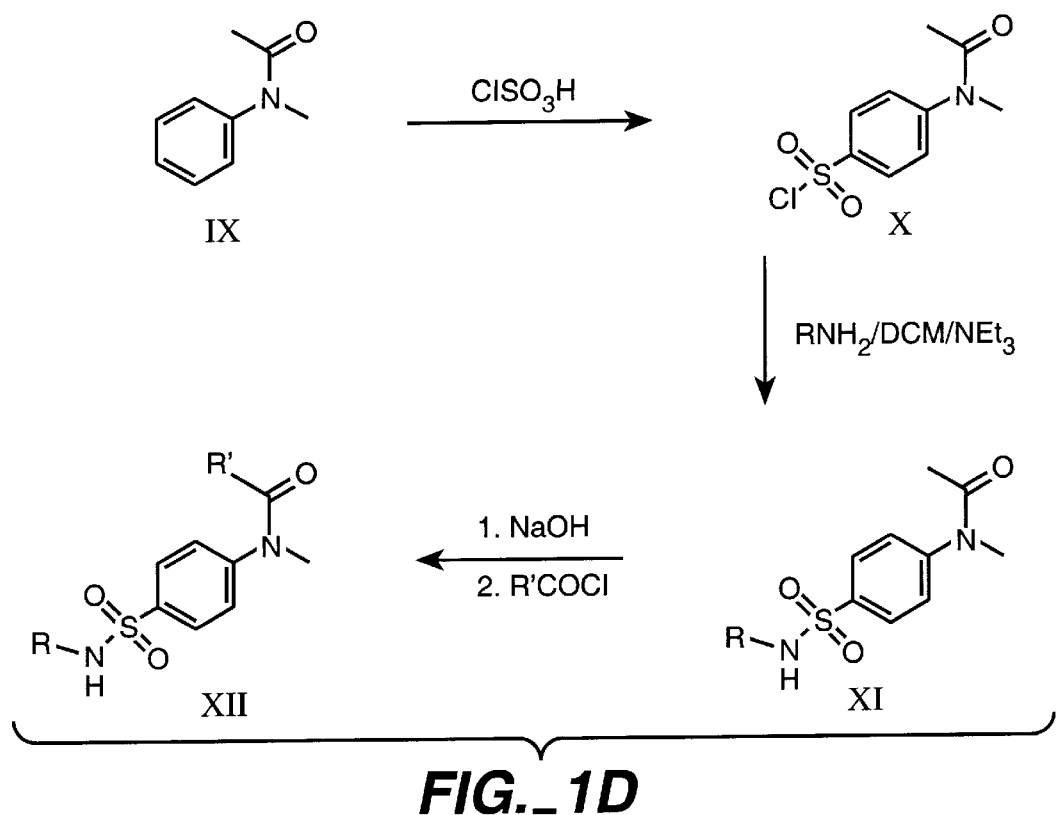
FIG._1D
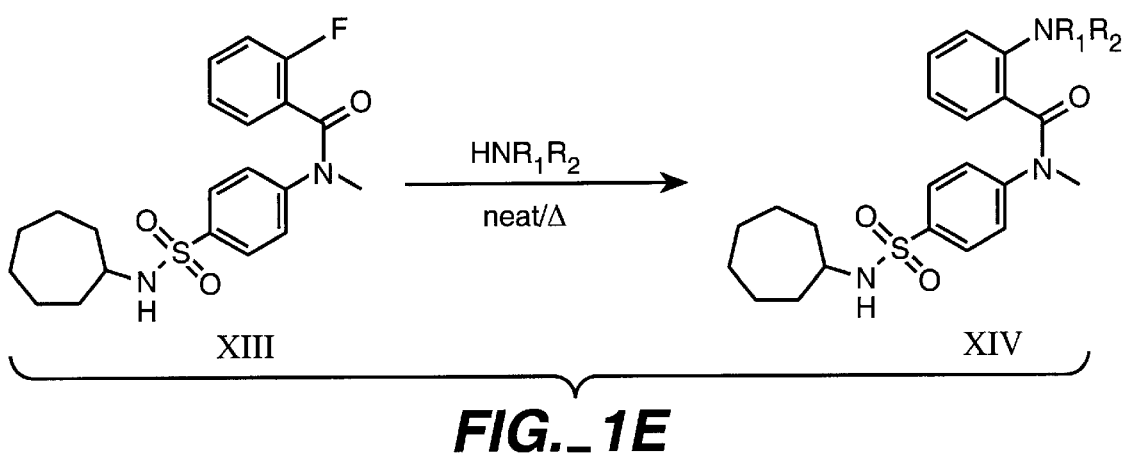
FIG._1E

ARYLSULFONAMIDES AS PHOSPHOLIPASE A₂ INHIBITORS

FIELD OF THE INVENTION

The present invention provides novel arylsulfonamides. These compounds have been found to inhibit phospholipase $A_2$ activity, in particular cPLA$_2$ (cytosolic phospholipase $A_2$). Additionally, the compounds inhibit the release of cytokines in stimulated cells. Still further, the compounds have been found to inhibit neurodegeneration in a mammalian neuronal cell population.

BACKGROUND OF THE INVENTION

Alzheimer's Disease

Alzheimer's disease (AD) is a progressive disease known generally as senile dementia. Broadly speaking the disease falls into two categories, namely late onset and early onset. Late onset, which occurs in old age (65+years), may be caused by the natural atrophy of the brain occurring at a faster rate and to a more severe degree than normal. Early onset AD is much more infrequent but shows a pathologically identical dementia with brain atrophy which develops well before the senile period, i.e., between the ages of 35 and 60.

Alzheimer's disease is characterized by the presence of numerous amyloid plaques and neurofibrillary tangles (highly insoluble protein aggregates) present in the brains of AD patients, particularly in those regions involved with memory and cognition. While in the past there was significant scientific debate over whether the plaques and tangles are a cause or are merely the result of AD, recent discoveries indicate that amyloid plaque is a causative precursor or factor. In particular, it has been discovered that the overproduction of β-amyloid peptide ("Aβ"), a major constituent of the amyloid plaque, can result from mutations in the gene encoding amyloid precursor protein, a protein which when normally processed will not produce the Aβ peptide.

One hypothesis regarding the pathogenesis of the disease is that deposition of Aβ peptide, which is the major macromolecular component of amyloid plaques, is the causative agent of the characteristic AD pathological changes leading to formation of neurofibrillary tangles, neuronal cell loss, vascular damage, and, ultimately, dementia (Hardy and Higgins (1992) *Science* 256: 184). Amyloid precursor protein (APP) is encoded by a single gene in humans. RNA transcripts of the APP gene are alternatively spliced to encode several APP protein isoforms; the predominant APP isoform in brain lacks a serine protease inhibitor domain that is present in other tissues. Aβ is a proteolytic cleavage product arising from the carboxy region of various APP isoforms, including the predominant APP isoform in the brain (U.S. Pat. No. 4,666,829; Glenner and Wong (1984) *Biochem. Biophys. Res. Commun.* 120: 1131; Kitaguchi et al. (1988) *Nature* 331: 530; Ponte et al., ibid., p.525; R. E. Tanzi, ibid., p.528; Kang and Muller-Hill (1990) *Biochem. Biophys. Res. Commun.* 166: 1192; Yoshioka et al. (1991) *Biochem. Biophys. Res. Commun.* 178: 1141; Johnson et al. (1990) *Science* 248: 854; Neve et al. (1990) *Neuron* 5: 329). The accumulation of extracellular Aβ results in insoluble amyloid deposits and may be neurotoxic, leading to neuronal death and neurofibrillary tangle formation.

Moreover, Aβ peptide appears to be toxic to brain neurons, and neuronal cell death is associated with the disease (Schubert et al. (1995) *Proc. Natl. Acad. Sci.* (USA) 92: 1989; Lorenzo and Yankner (1994) *Proc. Natl. Acad. Sci.* (*USA*) 91: 12243; Yankner et al. (1990) *Science* 250: 279; Kowall et al. (1991) *Proc. Natl. Acad. Sci.* (*USA*) 88: 7247; and Pike et al. (1993) *J. Neurosci.* 13: 1676). Mattson et al. (1992) *J. Neurosci.* 12: 376 and Mattson et al. (1993) *Trends in Neuroscience* 16: 409, report that Aβ and fragments thereof can destabilize calcium ($Ca^{+2}$) homeostasis in cultured human cortical neurons, and can render the neurons more susceptible to calcium ionophore-induced neurotoxicity. Meda et al. (1995) *Nature* 374: 647 report that Aβ and IFN-γ activates cultured microglial cells, leading to neuronal cell injury in co-cultured neurons. Both Meda et al. (1995) op.cit and Schubert et al. (1995) op.cit report the likely involvement of reactive free radical species, such as reactive nitrogen intermediates and reactive oxygen species.

Reports show that soluble Aβ peptide is produced by healthy neuronal cells in culture media (Haass et al. (1992) *Nature* 359: 322) and is present in human and animal cerebrospinal fluid (Seubert et al. (1992) *Nature* 359: 325). Thus, the mere presence of soluble Aβ peptide may not be sufficient for explaining the onset and progression of AD. However, aggregation and formation of insoluble complexes of Aβ have been implicated as having enhanced neurotoxicity to cultured neuronal cells.

To date, the exact molecular mechanisms which result in the characteristic pathology and neuronal deficits of Alzheimer's disease have not been described in the art. The development of experimental models of Alzheimer's disease that can be used to define further the underlying biochemical events involved in AD pathogenesis would be highly desirable. Such models could presumably be employed, in one application, to screen for agents that alter the degenerative course of Alzheimer's disease. For example, a model system of the biochemical events which contribute to the pathology of Alzheimer's disease could be used to screen for drugs or therapeutic regimens that reverse, arrest, or slow the pathogenesis and progression of AD. Presumably, such models could be employed to develop pharmaceuticals that are effective in preventing, arresting, or reversing AD.

Currently, there are no human pharmaceuticals which are known to be effective in inhibiting the development or progression of the degenerative CNS neuropathology of Alzheimer's Disease. U.S. Pat. No. 5,192,753 report that certain non-steroidal anti-inflammatory drugs useful in treating rheumatoid arthritis (e.g., indomethacin) are allegedly useful in reducing symptomatic progression in a selected group of five AD patients, but no effects on neuropathological progression were noted and the sample size and experimental methodology employed were insufficient to conclusively demonstrate efficacy. U.S. Pat. No. 5,137,873 disclose the use of tachykinin agonists to treat AD, although this approach has not proven successful in producing substantial amelioration of the progression of AD, and significantly more effective therapeutic agents are desired in the art.

There is a need in the art for new compounds having therapeutic use to treat or prevent Alzheimer's Disease and Aβ-related neurodegenerative diseases which have similar pathogenic mechanisms. The present invention provides such new compounds, compositions and methods of treatment.

SUMMARY OF THE INVENTION

The present invention provides novel arylsulfonamides which have the general structure:

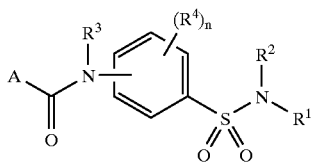

(I)

with the symbols $R^1$, $R^2$, $R^3$, $R^4$, A and n representing the groups and integers provided in the detailed description below. These compounds have activity as inhibitors of phospholipase A2, and in particular cytosolic phospholipase A2. The arylsulfonamides are also effective in inhibiting the release of cytokines in stimulated cells and in inhibiting neurodegeneration in a neuronal cell population. In view of these activities, these compounds are useful in the treatment of conditions associated with neurodegeneration, cytokine-mediated conditions (e.g., inflammation), and $PLA_2$-mediated conditions. The compounds and pharmaceutical compositions of the compounds are also useful in assays for other $PLA_2$ inhibitors.

BRIEF DESCRIPTION OF THE DRAWINGS

FIG. 1A–1E provides synthesis schemes for the compounds of the present invention.

DETAILED DESCRIPTION OF THE INVENTION

CONTENTS
I. Glossary
II. General
III. Arylsulfonamides
  A. Compounds
  B. Methods of Preparation
  C. Pharmaceutical Compositions
IV. Examples
V. Conclusion
I. Glossary Abbreviations and Definitions The term "Aβ peptide-mediated neurodegeneration" as used herein refers to degeneration of neuronal cells (e.g., cortical or hippocampal neurons, primary neuron cultures, neuronal cell lines) which is causally linked to accumulation of neurotoxic Aβ peptide; such toxicity may be manifested in the neuronal cells by direct interaction with toxic Aβ peptide or via indirect effects resulting from interaction of Aβ peptide with neuronal-associated cells (e.g., astrocytes, astrocytoma cells, microglial cells, monocytes, etc.). Such indirect effects may involve nitric oxide formation, excitatory amino acid mimetics, and/or cytokine production by the non-neuronal calls, whereby such compounds produce neuronal cell damage. Aβ peptide-mediated neurodegenerative diseases are exemplified, but not limited to, Alzheimer's Disease. Some neuropathologies may be causally associated with aberrant forms or amounts of other fragments or isoforms of the APP gene besides Aβ; these neuropathologies are also defined herein as Aβ peptide-mediated neurodegenerative diseases for purposes of this specification.

The term "neurodegeneration" as used herein refers to degeneration of neuronal cells (e.g., CNS neurons, primary neuron cultures, neuronal cell lines) which is causally linked to the accumulation of a neurotoxic substance (e.g., an amyloidogenic polypeptide other than Aβ) or a reduction of a necessary growth factor (e.g., NGF, BDNF, CTNF, etc.) which effects neuronal cell survival. Such neurodegeneration may be manifested in the neuronal cells by direct interaction with an amyloidogenic polypeptide other than Aβ peptide or via indirect effects resulting from interaction of an amyloidogenic polypeptide other than Aβ on neuronal-associated cells (e.g., astrocytes, astrocytoma cells, microglial cells, monocytes, etc.). Such indirect effects may involve nitric oxide formation, excitatory amino acid mimetics, and/or cytokine production by the non-neuronal calls, whereby such compounds produce neuronal cell damage. Some neuropathologies may be causally associated with aberrant forms or amounts of extracellular proteins other than Aβ; these neuropathologies are also defined herein as amyloidogenic polypeptide-mediated neurodegenerative diseases for purposes of this specification; for illustration, an example of such a type of neuropathology is Creutzfeldt-Jakob disease.

The term "active agent" is used herein to refer to an agent which inhibits $PLA_2$ activity, retards or reduces neurodegeneration, or inhibits cytokine release in cells. Active agents can be sold as commercial reagents for standardizing toxicological or pharmaceutical evaluations which employ neuron cultures or transgenic animals which exhibit neurodegenerative pathology. Some active agents will have therapeutic potential as drugs for human use, such as being administered to AD patients or individuals ascertained to be predisposed to developing AD or AD-type pathology (e.g., Down's Syndrome patients or familial AD). Some active agents will have therapeutic potential as drugs for human use, such as being administered to patients or individuals ascertained to be predisposed to developing degenerative neuropathology (e.g., Creutzfeldt-Jakob disease, Huntington's disease, stroke patients). The active agents described herein are all arylsulfonamides which in one mode of action selectively inhibit $PLA_2$. A selective inhibitor of $PLA_2$ produces a preferential inhibition of $PLA_2$ as compared to inhibition of other mammalian phospholipases; such that the concentration required to produce inhibition of 50% of $PLA_2$ catalytic activity is at least one order of magnitude lower than the concentration required to produce inhibition of 50% of the catalytic activity of phospholipases other than $PLA_2$. A selective inhibitor of $cPLA_2$ produces a preferential inhibition of $cPLA_2$ as compared to inhibition of other mammalian $PLA_2$ enzymes.

The term "$PLA_2$" as used herein refers to a naturally-occurring mammalian $PLA_2$ polypeptide having enzymatic activity. A paradigmatic $PLA_2$ can be considered to be human $cPLA_2$ substantially equivalent to that such as that described in U.S. Pat. Nos. 5,354,677 and 5,328,842; Clark et al. (1991) Cell 65: 1043, and Sharp et al. (1991) J. Biol. Chem. 266: 14850, or the cognate $cPLA_2$ enzyme in a non-human mammalian species. $PLA_2$ activity is present in a variety of cytosolic and extracellular $PLA_2$ polypeptide species. A preferred $PLA_2$ polypeptide of the invention is a cytosolic $PLA_2$, such as $cPLA_2$, and typically a calcium-activable $cPLA_2$ which is activated (exhibits enhanced catalytic activity) by the presence of calcium ions ($Ca^{+2}$).

The term "alkyl" refers to a cyclic, branched, or straight chain group typically containing only carbon and hydrogen, and unless otherwise mentioned, contain one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g., halogen, alkoxy, alkylthio, trifluoromethyl, acyloxy, hydroxy, mercapto, carboxy, aryloxy, aryl, arylalkyl, heteroaryl, heterocycle, amino, morpholino, piperidino, pyrrolidin-1-yl, piperazin-1-yl, or other functionality.

The term "lower alkyl" refers to a cyclic, branched or straight chain monovalent alkyl radical of one to six carbon atoms. This term is further exemplified by such radicals as methyl, ethyl, n-propyl, i-propyl, n-butyl, t-butyl, i-butyl (or 2-methylpropyl), cyclopropylmethyl, i-amyl, n-amyl, and hexyl.

The term "aryl" or "Ar" refers to a monovalent unsaturated aromatic carbocyclic group having a single ring (e.g., phenyl) or multiple rings either condensed rings (e.g., naphthyl or anthryl), linked covalently (e.g., biphenyl) or linked to a common group such as an ethylene or methylene moiety (e.g., diphenylmethyl). The aromatic rings can optionally be unsubstituted or substituted with, e.g., halogen, alkyl, alkoxy, alkylthio, trifluoromethyl, acyloxy, hydroxy, mercapto, carboxy, aryloxy, arylalkyl, heteroaryl, heterocycle, amino, morpholino, piperidino, pyrrolidin-1-yl, piperazin-1-yl, or other functionality. The term "aryl" is also meant to include "heteroaryl" or "HetAr" which is an aromatic heterocycle (e.g. pyridine, quinoline, quinoxaline, thiophene, furan, pyrrole and the like).

The term "alkoxy" refers to a group having the structure —O—R, where R is alkyl, as described above, which may be substituted with a non-interfering substituent. The term "arylalkoxy" refers to a group having the structure —O—R—Ar, where R is alkyl and Ar is an aromatic substituent. Arylalkoxys are a subset of substituted alkoxys. Examples of preferred substituted alkoxy groups are: benzyloxy, napthyloxy, and chlorobenzyloxy.

The term "aryloxy" refers to a group having the structure —O—Ar, where Ar is an aryl group. A preferred aryloxy group is phenoxy.

The term "heterocycle" refers to a monovalent saturated, unsaturated, or aromatic carbocyclic group having a single ring (e.g., morpholino, pyridyl or furyl) or multiple condensed rings (e.g., indolizinyl or benzo[b]thienyl) and having at least one heteroatom, defined as N, O, P, or S, within the ring, which can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

"Arylalkyl" refers to the groups —R—Ar and —R—HetAr, where Ar is an aryl group, HetAr is a heteroaryl group, and R is straight-chain or branched-chain aliphatic group. Examples of arylalkyl groups include benzyl and furfuryl. Arylalkyl groups can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, morpholino, piperidino, pyrrolidin-1-yl, piperazin-1-yl, or other functionality.

As used herein, the term "halo," "halogen atom" or "halide" refers to fluoro, bromo, chloro and iodo substituents.

As used herein, the term "amino" refers to a chemical functionality—$NR^aR^b$, where $R^a$ and $R^b$ are independently hydrogen, alkyl, or aryl. The term "quaternary amine" refers to the positively charged group —$N^+R^aR^bR^c$, where $R^a$, $R^b$, and $R^c$ are independently selected and are alkyl or aryl. A preferred amino group is —$NH_2$.

The term "pharmaceutical agent or drug" as used herein refers to a chemical compound or composition capable of inducing a desired therapeutic effect when properly administered to a patient.

Other chemistry terms herein are used according to conventional usage in the art, as exemplified by *The McGraw-Hill Dictionary of Chemical Terms* (ed. Parker, S., 1985), McGraw-Hill, San Francisco, incorporated herein by reference).

II. General

Overview

A basis of the present invention is the unexpected finding that certain arylsulfonamides possess a variety of therapeutically useful activities. In particular, the arylsulfonamides described herein exhibit one or more of the following activities: inhibition of $PLA_2$ activity, inhibition of neuronal cell degeneration, and inhibition of cytokine release. While certain conditions may have physiological basis in two or more of the above described activities ($PLA_2$ activity, neuronal cell degeneration and cytokine release), the present invention is not so limited. In particular, the compounds described herein will find application in each of the conditions modulated by at least one of the recited activities. Thus, the compounds are useful in conditions mediated by $PLA_2$ activity, as well as those conditions mediated by cytokine release and those conditions normally associated with neuronal cell degeneration. For example, neuronal degeneration, such as that which results from exposure of neuronal cells to pathogenic forms of Aβ or amyloidogenic protein as occurs in Alzheimer's Disease and other neurodegenerative conditions can be treated with the compounds described herein.

Neurodegenerative Disease

Neurodegenerative diseases are believed to comprise a broad variety of neurodegenerative diseases. For example and not to limit the invention, neurodegenerative diseases are exemplified, but not limited to: Lewy Body disease, degeneration resultant from cerebral ischemia, ALS, prion-related disease (Creutzfedlt-Jakob, kuru, etc.), Parkinson's disease, multiple sclerosis, hereditary ataxia, Shy Drager Syndrome, Progressive Supranuclear Palsy, Huntington's disease, spinal muscular atrophy (Types I, II, and III), Reye's Syndrome, status epilepticus, progressive multifocal leukoencephalopathy, viral encephalitis, normal pressure hydrocephalus, subacute sclerosing panencephalitis, head and spinal cord trauma post-injury degeneration, frontal lobe dementia, poliomyelitis and postpolio neuropathy, glaucoma, and various neuropathies (autonomic, Guillan-Barre, diabetic, porphyria, autoimmune, vasculitis, among others.

Neurodegenerative diseases associated with amyloidogenic polypeptides include but are not limited to:
Prion-related diseases (e.g., Creutzfeldt-Jakob disease, scrapie, Kuru);
Transthyretin (TTR)-induced polyneuropathies (including, but not limited to:
Portuguese, Japanese, Swedish, Illinois-German, Swiss-Indiana, Maryland-German, Appalachian-Israel);
ApoA1-induced polyneuropathy (e.g., Iowa variant);
Gelsolin-induced polyneuropathy (e.g., Finnish variant);
Icelandic Hemorrhage angiopathy due to cystatin C disease;
Serum AA amyloid polyneuropathy as seen in familial Mediterranean fever, and other conditions that case AA amyloidosis, such as leprosy, tuberculosis, rheumatoid arthritis; and Immunoglobulin/light chain amyloid polyneuropathy as seen in multiple myeloma and primary amyloidosis; among others. It is believed that these diseases and other neurodegenerative diseases can be treated by administration of a therapeutically efficacious dose of a suitable $PLA_2$ inhibitor. Such administration will often require chronic dosing. Other neurodegenerative diseases are described in: 19th Edition: Cecil Textbook of Medicine, Wyngaarden, Smith and Bennett, eds. pp. 1141–1145, 1992, W. B. Saunders, Philadelphia, Pa.

Cytokine-Mediated Conditions

The term "cytokine-mediated conditions" refers to disease states in which excessive or unregulated IL-1 or TNF production by monocytes and/or macrophages is implicated in exacerbating and/or causing the disease. IL-1 or TNF production by monocytes and/or macrophages, as used herein, refers to the in vivo release of IL-1 or TNF by such cells. Examples of the above cytokine-mediated conditions include rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, fever and myalgias due to infection, such as influenza, cachexia secondary to infection or malignancy, cachexia secondary to acute immune deficiency syndrome (AIDS), keloid formation, scar tissue formation, Crohn's disease, ulcerative colitis, or other inflammatory skin conditions such as pyresis.

Alzheimer's Disease

Cellular models of Alzheimer's Disease (AD) neuropathology are based on the ability of the Alzheimer's Disease-associated Aβ peptide to induce biological changes (e.g., microglia and astrocyte activation, monocyte activity, neuronal degeneration) in cultured human and rodent cell populations (neurons, neuronal cell lines, microglia, microglial cell lines, astrocytes, astrocytoma cells and cell lines, monocytes and monocytic cell lines) and neuronal and glial cell lines, wherein the biological changes mimic the neuropathological changes associated with Alzheimer's Disease.

A basis of the invention underlying application Ser. No. 08/486,392 and U.S. Pat. No. 5,478,857 was the unexpected observation that several structurally dissimilar inhibitors of $PLA_2$ were capable of inhibiting Aβ-mediated or amyloidogenic protein-mediated microglial activation and Aβ-mediated neuronal degeneration in such cellular models of AD. Based on that observation and others made therein, it is now believed that $PLA_2$ activity is an essential component of Aβ-mediated and amyloidogenic-mediated neuropathological changes, such as those which occur in AD, Down's Syndrome, and other neurodegenerative diseases. Active agents which inhibit $PLA_2$ activity are expected to inhibit neuropathological changes.

Phospholipase $A_2$

Phospholipases $A_2$ ($PLA_2$s; EC 3.1.1.4) are enzymes that hydrolyze the 2-acyl ester bond of phosphoglycerides generating free fatty acids and lysophospholipids (for review, see, Kramer, R M (1993) *Advances in Second Messenger and Phosphoprotein Research* 28: 81; Glaser et al. (1993) *TiPS* 14: 92; Dennis E A (1994) *J. Biol. Chem.* 269: 13057). $PLA_2$s are a diverse class of enzymes with regard to function, localization, regulation, mechanism, sequence, structure, and role of divalent metal ions.

In general, $PLA_2$ enzymes catalyze the hydrolysis of the fatty acid ester bond at the sn-2 position of membrane phospholipids to produce arachidonic acid and its metabolites. A variety of polypeptide species can exhibit $PLA_2$ activity; for purposes of this specification, these polypeptides are considered $PLA_2$ isozymes.

Group I, II, and III $PLA_2$s are extracellular enzymes of approximately 14–18 kD in humans, and are designated $sPLA_2$s, in recognition of their secretion. $sPLA_2$s are found in many extracellular fluids and have a broad substrate specificity for many types of phospholipids.

Group IV $PLA_2$ is a cytosolic enzyme of approximately 85 kD (based on deduced cDNA coding sequence) to 110 kD (based on SDS-PAGE of purified protein), and is designated $cPLA_2$ to indicate its cytosolic location. Unlike $sPLA_2$s, the $cPLA_2$ enzyme exhibits preferential catalysis of phospholipids which contain arachidonic acid, and is most likely the enzyme responsible for arachidonic acid release which is the rate-limiting step for subsequent eicosanoid biosynthesis of pro-inflammatory lipid mediators (prostaglandins, leukotrienes, lipoxins, and platelet-activating factor: "PAF").

In addition to the $cPLA_2$ of U.S. Pat. No. 5,322,776, some cells contain calcium independent phospholipase $A_2$/B enzyme. The purified enzyme is characterized by activity in the absence of calcium and molecular weight of 86 kD on SDS-PAGE (see U.S. Pat. Nos. 5,554,511 and 5,466,595).

Other $PLA_2$ activities, both cytosolic and extracellular, are less well-characterized with regard to macromolecular identification and polypeptide sequences.

$cPLA_2$ is present in the cytosol of a variety of species and cell types, including human U937 cells (monocytes), platelets, kidney, and macrophages, among others, and is implicated in controlling arachidonic acid metabolism and eicosanoid production.

Human $cPLA_2$ has been cloned as a cDNA isolated from mRNA of a human monocytic cell line (U.S. Pat. Nos. 5,354,677 and 5,328,842; Sharp et al. (1991) op.cit, Clark et al. (1991) op.cit) and the mRNA encodes a protein of 749 amino acids which has little detectable homology with the secreted $sPLA_2$s or any other protein in known sequence databases. The $cPLA_2$ cDNA identifies a single copy gene in the human genome, with no detectable closely related genes based on Southern blotting experiments.

$cPLA_2$ contains an amino-terminal domain which binds calcium and similar divalent cations, and $cPLA_2$ binds to membrane vesicles at submicromolar concentrations of $Ca^{+2}$ in a calcium-dependent fashion. $cPLA_2$ can translocate to membranes when activated in the presence of calcium. Presumably, $cPLA_2$ associates with membrane components in vivo under suitable calcium concentrations. Agents that stimulate the release of arachidonic acid (ATP, thrombin, phorbol ester, calcium ionophore) can cause increased serine phosphorylation of $cPLA_2$ which increases the enzymatic activity of $cPLA_2$ (Lin et al. (1993) *Cell* 72: 269). Phosphorylation is believed to contribute to the control of $cPLA_2$ activity in vivo (Lin et al. (1992) *Proc. Natl. Acad. Sci.* (*USA*) 89: 6147; Lin et al. (1993) *Cell* 72: 269; Qiu et al. (1993) *J. Biol. Chem.* 268: 24506; Kramer et al. (1993) *J. Biol. Chem.* 268: 26796).

Antibodies have been raised against human $cPLA_2$ and crossreact with $cPLA_2$ from a variety of animals, indicating conservation of structure between species. Anti-$cPLA_2$ antibodies identify the presence of $cPLA_2$ in lung, brain, testis, kidney, spleen, liver, and heart, although the precise role of $cPLA_2$ in the metabolism of each of these tissues is not known.

The art generally recognizes the physiologic role of $cPLA_2$ to be in the mediation of inflammation via its role in arachidonic acid metabolism and lipid/lipoprotein metabolism, such as cell membrane homeostasis. Roshak et al. (1994) *J. Biol. Chem.* 269: 25999 used antisense oligonucleotides complementary to the cPLA$_2$ mRNA to inhibit prostaglandin production in LPS-induced monocytes, indicating a potential role for cPLA$_2$ in generating inflammatory regulators in monocytes. Verity M A (1993) *Ann. N. Y Acad. Sci.* 679: 110 speculates that "abusive activation" of PLA$_2$ via uncontrolled Ca$^{+2}$ influx might produce irreversible cell injury of neurons via extensive localized lipid peroxidation and subsequent membrane disintegration. U.S. Pat. Nos. 5,354,677 and 5,328,842 indicates that cPLA$_2$ inhibitors are expected to be used to treat inflammatory conditions, such as psoriasis, asthma, and arthritis (see, col. 15), and prophesizes that such anti-inflammatory compounds can be identified as cPLA$_2$ inhibitors.

A number of inhibitors of PLA$_2$ activity have been reported. Bromoenol lactone and trifluoromethyl ketones (e.g., palmitoyl trifluoromethyl ketone, arachidonyl trifluoromethyl ketone) have been reported to be capable of inhibiting a Ca$^{+2}$-independent PLA$_2$ activity (Ackermann et al. (1995) *J. Biol. Chem.* 270: 445) as well as cPLA$_2$ (Street et al. (1993) *Biochemistry* 32: 5935). Several benzenesulfonamide derivatives have also been reported to be capable of inhibiting PLA$_2$ activity (European Patent Application 468 054; Oinuma et al. (1991) *J. Med. Chem.* 34: 2260).

Reynolds et al. (1994) *Anal. Biochem.* 217: 25 describe a convenient microtiter plate assay for cPLA$_2$. Currie et al. (1994) *Biochem. J.* 304: 923, describe a cPLA$_2$ assay for assaying cPLA$_2$ activity from activated whole cells. This assay can be adapted for assay of related PLA$_2$ activity, whether from cPLA$_2$ or other PLA$_2$ enzymes having similar catalytic activities.

A suitable source of cPLA$_2$ can be obtained, if desired, by expression of a recombinant expression vector in a suitable host cell, as described in U.S. Pat. No. 5,354,677, or by conventional biochemical purification from mammalian cells, as is known in the art.

In view of our earlier discoveries (see Ser. No. 08/486,392) we have now identified other arylsulfonamides which are effective inhibitors of PLA$_2$, more particularly cPLA$_2$. We have further discovered that these compounds inhibit cytokine release. Still further, we have determined that these compounds are suitable for mediating neurodegeneration in a neuronal cell population.

III. Arylsulfonamides

A. Compounds

The present invention provides compounds which are useful for the inhibition of phospholipase A2. In particular, the invention provides arylsulfonamides having the formula:

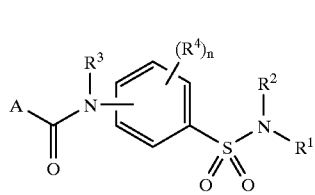

(I)

In this formula, the letter A represents a C$_4$–C$_{10}$ alkyl group, an aryl group (including heteroaryl), an arylalkyl group, radicals of formulae: —CH=CH—B, —O—B, —S—B, —NH—B, or —CH$_2$—X. For the radicals described, B represents a non-aromatic C$_3$–C$_8$ carbocycle, a C$_3$–C$_8$ alkyl group, a heterocycle or an arylalkyl group, each of which is optionally substituted with one or more members independently selected from the group consisting of a halogen atom, a C$_1$–C$_4$ alkyl group, a C$_1$–C$_4$ alkoxy group, cyano, nitro, amino, a heterocycle, an aryl group and an aryloxy group. Additionally, X is a halogen atom, —S—aryl, —S—heterocycle, or —PO$_3$R$_2$ wherein each R is independently a hydrogen atom or C$_1$–C$_3$ alkyl.

R$^1$ and R$^2$ may be the same or different from each other and each stand for a hydrogen atom, a lower alkyl group, a group represented by the formula: —(CH$_2$)$_q$—A', wherein q is an integer of 2 to 4; and A' stands for a hydroxyl group or a group represented by the formula:

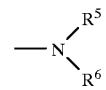

(wherein R$^5$ and R$^6$ may be the same or different from each other and each stand for a hydrogen atom or a lower alkyl group). A' can also be a group represented by the formula:

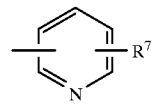

(wherein R$^7$ stands for a hydrogen atom or a lower alkyl group) or a group represented by the formula:

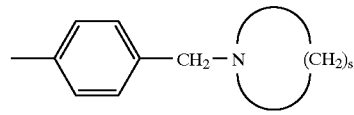

wherein s is an integer of 2 to 5).

In yet other embodiments, R$^1$ or R$^2$ can be an unsubstituted or substituted cycloalkyl group, a bicycloalkyl, tricycloalkyl or azabicycloalkyl group or a group represented by the formula:

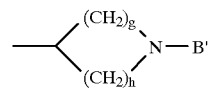

(wherein g and h are each an integer of 1 to 4; and B' stands for a lower alkyl group, a substituted or unsubstituted arylalkyl group or a substituted or unsubstituted pyridyl alkyl group).

Alternatively R$^1$ and R$^2$ may be combined together to form a 6- or 7-membered ring which may contain a nitrogen or oxygen atom in addition to the nitrogen atom to which R$^1$ and R$^2$ are bonded, and the 6- or 7-membered ring may be substituted with a lower alkyl, arylalkyl, cycloalkylalkyl or heteroarylalkyl group.

A plurality of R$^4$ groups each independently stand for a hydrogen atom, a lower alkyl group, a lower alkoxy group or a halogen atom; and n is an integer of from 1 to 4, provided that when n is 2, the two R$^4$ groups may form a ring together with two adjacent carbon atoms constituting the benzene ring. Among the groups defined with respect to R$^4$, a hydrogen atom is most desirable, i.e., the benzene ring is most desirably an unsubstituted one. As noted, when n is 2, the two R$^4$ groups may form a ring together with adjacent two carbon atoms constituting the benzene ring. Particular examples of such a ring are as follows:

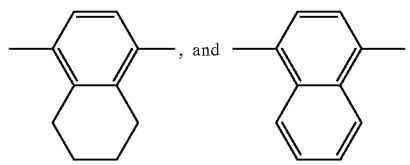, and

The symbol $R^3$ represents a hydrogen atom, a lower alkyl group, or a $C_3$–$C_8$ cycloalkyl group. Preferably, $R^3$ is a lower alkyl group, more preferably methyl or ethyl. Additionally, the compounds provided by the above formula (I) will include any pharmacologically acceptable salts thereof.

In the above definition of the compound (I) according to the present invention, the lower alkyl group defined with respect to $R^1$, $R^2$, $R^3$, $R^4$, $R^7$ and B' is a straight chain or branched alkyl group having 1 to 6 carbon atoms. Methyl, ethyl, propyl and isopropyl groups are preferred, among which the methyl group is most preferred.

The lower alkoxy group is one derived from the above-mentioned lower alkyl group having 1 to 6 carbon atoms and preferable examples thereof include methoxy, ethoxy, n-propoxy, isopropoxy and n-butoxy groups.

The heteroaryl group is a group derived from a heterocycle containing one or more nitrogen, oxygen or sulfur atoms. Particular examples thereof include pyridyl, furyl and imidazolyl groups.

Among the groups represented by the formula:

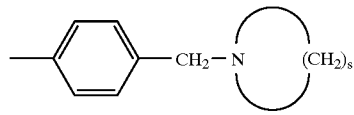

(wherein s is an integer of 2 to 5) in the definition of $R^1$ and $R^2$, a group represented thereby wherein s is 4 or 5 is most desirable.

The unsubstituted cycloalkyl group defined with respect to $R^1$ and $R^2$ includes cyclopropyl, cyclobutyl, cyclopentyl, cyclohexyl, cycloheptyl, cyclooctyl, cyclononyl, cyclodecyl and cyclododecyl groups. Preferably, the unsubstituted cycloalkyl group is a cycloheptyl group.

The substituted cycloalkyl group is a cycloalkyl group as described above which is either substituted with a lower alkyl group such as a methyl group or a halogen atom or condensed with an aromatic ring such as a benzene ring or a heterocyclic ring such as a pyridine ring at adjacent carbon atoms constituting the cyclcoalkyl group to form a condensed ring group represented by the formula:

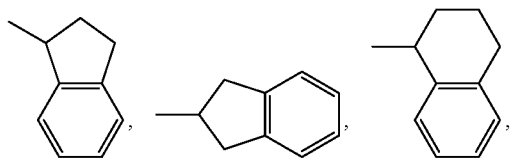

-continued

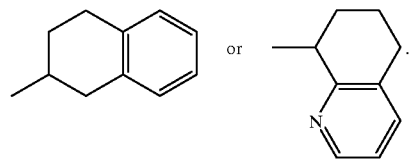

The bicycloalkyl or tricycloalkyl group is an aliphatic saturated hydrocarbon group which is composed only of two or three rings with at least two carbon atoms being jointly owned by the rings.

Representative examples of the bicycloalkyl group include

The tricycloalkyl group is, for example, an adamantyl group.

The azabicycloalkyl group is a bicycloalkyl group described above in which one of the carbon atoms constituting the bicycloalkyl group is replaced by a nitrogen atom. Examples thereof include

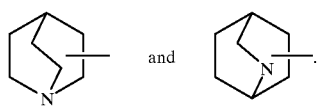

In the formula:

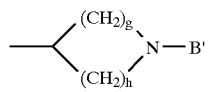

in the definition of $R^1$ and $R^2$, g and h are each an integer of 1 to 4. Examples of the group represented by the formula include

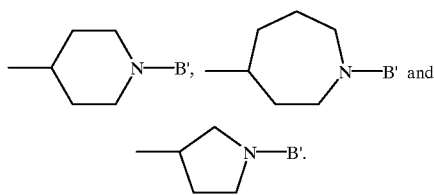

The substituted or unsubstituted arylalkyl group defined with respect to B' is one derived from an aryl group (such as a phenyl or naphthyl group) which may be substituted with a lower alkyl group such as a methyl or ethyl group, a halogen atom or a lower alkoxy group such as a methoxy group and examples thereof include benzyl and phenethyl groups. Further, the substituted or unsubstituted pyridylalkyl group defined with respect thereto is one derived from a pyridyl group which may be substituted with a lower alkyl group such as a methyl or ethyl group, a halogen atom or a lower alkoxy group such as a methoxy group. Preferred examples of the group represented by the above formula include

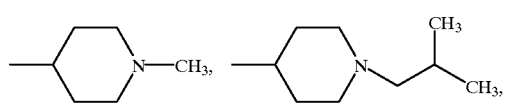

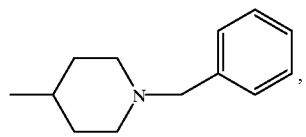

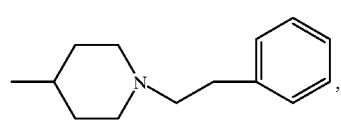

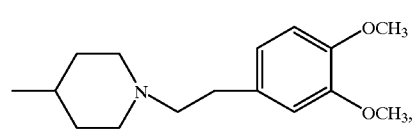

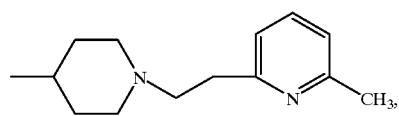

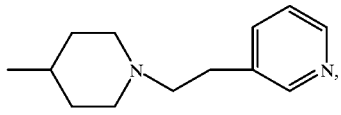

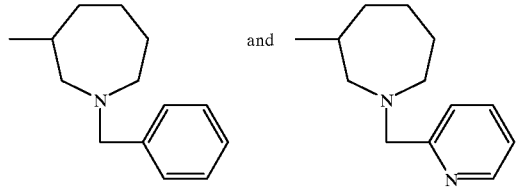

Preferred examples of the 6- or 7-membered ring formed by the groups $R^1$ and $R^2$ which may contain a nitrogen or oxygen atom in addition to the nitrogen atom to which the groups are bonded are as follows:

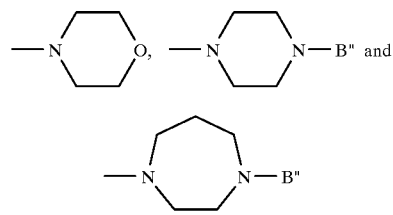

These 6- or 7-membered rings may be each substituted with a B" group such as a lower alkyl, arylalkyl, cycloalkylalkyl or heteroarylalkyl group. The arylalkyl, cycloalkylalkyl and heteroarylalkyl groups are each the same as that defined above.

Particular examples thereof are as follows:

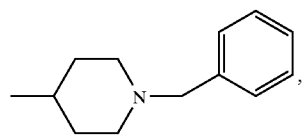

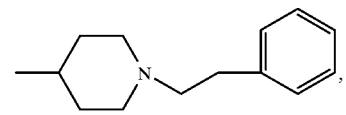

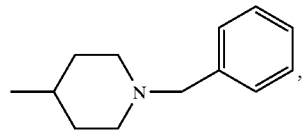

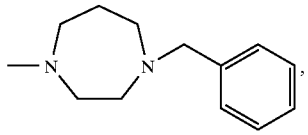

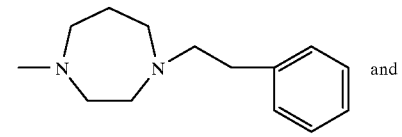

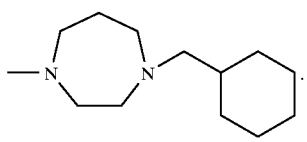

B. Methods of Preparation

The arylsulfonamides provided above can be prepared using standard synthetic methods as outlined in FIGS. 1A–1E. Briefly, the starting materials in these methods, for example, N-cycloheptyl-4-(N-methylamino) benzenesulfonamide II (or other substituted benzenesulfonamides) can be prepared as described in U.S. Pat. No. 5,281,626, incorporated herein by reference.

According to the method outlined in FIG. 1A, the starting benzenesulfonamide II is acylated with a suitable acid chloride III in an organic solvent using a base such as triethylamine, pyridine, DBU, diisopropylethylamine and related amine bases to produce the desired arylsulfonamides IV.

Alternatively, the starting benzenesulfonamide II can be acylated with bromoacetyl chloride (see FIG. 1B), to produce the bromoacetamide derivative V. Treatment of V with triethylphosphite (Arbusov reaction) provides a phosphonate VI which can be reacted with an appropriate aldehyde in a classical Horner-Emmons reaction (Wadsworth, et al., Org. React. 25:73–253 (1977)) to give the corresponding vinylogous amide (VII). The bromoacetamide can also be converted to a thioether VIII (see FIG. 1C) using an appropriate thiol in the presence of $ZnI_2$.

FIG. 1D provides yet another synthetic scheme for the preparation of novel arylsulfonamides. According to this scheme, N-acetyl-N-methylaniline IX is sulfonated with chlorosulfonic acid using literature procedures to provide X. Treatment of the resultant sulfonyl chloride X with a suitable amine in an organic solvent containing either a tertiary amine as an HCl scavenger or a second equivalent of the primary or secondary amine provides the sulfonamide XI.

Removal of the acetyl group and re-acylation with another acid chloride follows standard procedures to provide XII.

A number of compounds of the present invention can be prepared by suitable conversions of related compounds (which are also within the scope of the present invention). One example is provided in FIG. 1E. In this figure a fluorobenzamide derivative XIII is heated with a secondary amine, in the absence of solvent to provide an amine-substituted benzamide XIV. Other conversions will be known to those of skill in the art, based on the examples provided below.

C. Pharmaceutical Compositions

Active agents which inhibit neuronal degeneration in disease models can be used to retard or reduced neuropathology in vivo. Additionally, those agent which inhibit $PLA_2$ activity can be used for the treatment of conditions mediated by $PLA_2$. Still further, in view of the agents' modulation of cytokine release, the agents will also find use in mediating conditions modulated by cytokines. Thus, the present invention further comprises pharmaceutical compositions incorporating one or more of the arylsulfonamides described herein in a pharmaceutically acceptable carrier. Such pharmaceutical compositions should contain a therapeutic or prophylactic amount of at least one arylsulfonamide. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, *Remington's Pharmaceutical Sciences*, Mack Publishing Company, Easton, Pa., 16th Ed., 1982, the disclosure of which is incorporated herein by reference.

The pharmaceutical compositions just described are suitable for systemic administration to the host, including both parenteral, topical, and oral administration, including intracranial administration. Thus, the present invention provides compositions for administration to a host, where the compositions comprise a pharmaceutically acceptable solution of the identified inhibitory compound in an acceptable carrier, as described above. Such formulations can be used therapeutically on mammals having AD-type neuropathology or disease progression of a related neurodegenerative disease.

Compositions containing the present inhibitors (or active agents) can be administered for prophylactic and/or therapeutic treatments of neurodegenerative disease. In therapeutic application, compositions are administered to a patient already affected by the particular neurodegenerative disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration, but generally range from about 1 mg to about 10 g of $PLA_2$ inhibitor per dose, with dosages of from 10 mg to 2000 mg per patient being more commonly used. Suitable concentrations (i.e., efficacious dose) can be determined by various methods, including generating an empirical dose-response curve, predicting potency and efficacy of a congener by using QSAR methods or molecular modeling, and other methods used in the pharmaceutical sciences.

The compositions for parenteral administration will commonly comprise a solution of an active agent or a cocktail thereof dissolved in an acceptable carrier, preferably an aqueous carrier or organic solvent (e.g., DMSO, solvated PEG, etc.). Since many of the active agents of the invention can be lipophilic or latentiated, it is preferable to include in the carrier a hydrophobic base (e.g., polyethylene glycol, Tween 20). A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the active agent in these formulations can vary widely, i.e., from less than about 1 nM, usually at least about 0.1 mM to as much as 100 mM and will be selected primarily based on fluid volumes, viscosities, etc., in accordance with the particular mode of administration selected. Most usually, the active agent is present at a concentration of 0.1 mM to 5 M. For example, a typical formulation for intravenous or intracranial injection comprises a sterile solution of an active agent at a concentration of 1–500 mM in Ringer's solution. The generally hydrophobic nature of some of the active agents indicates that a hydrophobic vehicle may be used, or that an aqueous vehicle comprising a detergent or other lipophilic agent (e.g., Tween, NP-40, PEG); alternatively, the active agents may be administered as a suspension in an aqueous carrier, or as an emulsion.

Thus, a typical pharmaceutical composition for intramuscular injection could be made up to contain 10 mL sterile buffered water, and about 1–1000 mg of active agent. A typical composition for intravenous infusion can be made up to contain 250 mL of sterile Ringer's solution, and about 100–5000 mg of active agent. Lipophilic agents may be included in formulations. Actual methods for preparing parenterally administrable compositions will be known or apparent to those skilled in the art and are described in more detail in, for example, *Remington's Pharnnaceutical Science*, 15th Ed., Mack Publishing Company, Easton, Pa. (1980), which is incorporated herein by reference.

The invention also provides the use of an arylsulfonamide of the present invention to slow, arrest, or reverse the development of a neurodegenerative disease such as Alzheimer's disease or Down's Syndrome in a human patient. In these uses an efficacious amount of the compound is administered to the patient to inhibit progression of the disease.

The invention also provides the use of an arylsulfonamide to slow, arrest, or reverse the development of a neurodegenerative disease in a human patient. In these uses an efficacious amount of the compound is administered to the patient to inhibit progression of the disease.

VI. Examples

A. Assays for Determining Biological Activity

The $PLA_2$ inhibitory properties of the compounds of the present invention are evaluated using following assays. Inhibition of release of $[^{14}C]$-AA from phosphatidylcholine was measured as described. Human U937 cells are cultured in RPMI 1640 medium supplemented with 10% fetal bovine serum, penicillin, L-glutamine, and HEPES buffer. Cells are harvested and washed 3 times with extraction buffer (140 mM NaCl–5 mM KCl–2 mM EDTA–25 mM Tris pH 7.4) and resuspended at $1 \times 10^8$ cells/mL containing 100 μM leupeptin–50 μM pepstatin–1 μmM PMSF. Cells are placed in a N₂ cavitation bomb and put under pressure at 600 psi or maximum pressure for 20 minutes at 4° C. Cells are then released. The suspension is collected and spun at 100,000 g for 60 minutes at 4° C. Supernatant is collected and filtered through a 0.22 μm filter. Extract is then diluted to 50% glycerol and stored at −20° C.

For the preparation of substrate, 20 nmol of phosphatidylcholine-α-1-palmitoyl-2-arachidonyl-1-[$^{14}$C] and 10 nmol 1,2-dioleyl-glycerol are mixed together and dried under a N₂ stream. A solution of 1 mL of 150 mM NaCl–50 mM HEPES pH 7.5 is added to mixture. To reconstitute liposomes, the mixture is then sonicated with Branson 450 sonifier for 2 minutes at 50% duty cycle output level 3 on ice. After sonification, 40 μL of a 100 mg/mL BSA solution is added.

The compounds were first dissolved in DMSO at 2mM and serially diluted in DMSO by a factor of five for a total of 5 concentrations. These dilutions are further dissolved 60 fold in reaction buffer (150 mM NaCl–50 mM HEPES pH 7.5–1 mM CaCl₂–1 mM 2-ME) containing approximately 5% of the U937 cytosolic extract to make up the preincubation mixture which is then incubated for 20 minutes at 37° C. Vehicle control using only DMSO with no compound is also made. To 30 μL of this Extract/compound mixture is added 10 μL of substrate. This 40 μL reaction mixture is incubated for 15 minutes at 37° C. and the reaction is stopped by adding 400 μL Dole's reagent [2-propanol/heptane/0.5 M H₂SO₄ (40:10:1) 10 μg/mL stearic acid]. This is followed by the addition of 240 μL heptane and 200 μL water. 280 μL of the top heptane layer is transferred to a tube containing 60 mL silica gel with 200 μL heptane and mixed vigorously. Silica gel is then centrifuged down at 1000 g for 1 minute. 400 μL of liquid is transferred to scintillation vial along with 4 mL of Beckman Ready Safe scintillation cocktail and mixed. Vials are read in Beckman scintillation counter.

B. Synthesis of Representative Compounds

General Methods and Procedures

All operations were carried out at room or ambient temperature, that is, at a temperature in the range of 18–25° C.; evaporation of solvent was carried out using a rotary evaporator under reduced pressure (600–4000 pascals: 4.5–30 mmHg) with a bath temperature in the range of up to 60° C.; the course of the reaction was followed by thin layer chromatography (TLC) and reaction times are given for illustration only; melting points given are uncorrected and are obtained for materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 300 MHz using the indicated solvent; conventional abbreviations used for signal shape are: s, singlet; d, doublet; t, triplet; m, multiplet; br, broad; etc. : in addition chemical symbols have their usual meanings; the following abbreviations have also been used v (volume), w (weight), mp (melting point), L (liter(s)), mL (milliliters), g (gram(s)), mg (milligram(s)), mmol (millimoles), eq (equvalent(s).

The following abbreviations have the indicated meanings: Et₃N, triethylamine; Ac, acetyl; DMF, N,N-dimethylformamide; Ph, phenyl; r.t., room temperature; and TLC, thin layer chromatography.

Procedure A—Acylation of the sulfonamide (FIG. 1A)

To a solution of the sulfonamide in dichloromethane (DCM) was added 1 equivalent of triethylamine with stirring at 0° C. The acid chloride was slowly added to this mixture. The reaction was allowed to stir at room temperature for 8 hrs. The reaction was worked up by partitioning between water and ethyl acetate, the organic layer was separated, washed with brine, and dried over sodium sulfate. The crude product residue was purified by chromatography.

Procedure B—Horner-Emmons reaction (FIG. 1B)

A mixture of the phosphonate (1 mmol) in 5 mL tetrahydrofuran (THF) and 1.3 equivalents of sodium hydride was stirred under nitrogen until a clear yellow solution was obtained. To this mixture was added 1.5 equivalents of the aldehyde and the reaction was stirred at room temperature for 2 hours. The reaction was worked up by partitioning between 1N HCl and ethyl acetate. The organic layer was dried over sodium sulfate and crude product was purified by chromatography. (Wadsworth et. al., *Org. React.* 25:73–253 (1977)).

Procedure C—Displacement of bromide (FIG. 1B)

A mixture of the bromide (3.5 mmol) in 30 mL of toluene and 1.5 equivalents of triethylphosphite in 30 mL of toluene was refluxed for 17 hrs. The reaction was worked up by partitioning between water and ethyl acetate, the organic layer was separated, washed with brine, and dried over sodium sulfate. Product was purified by chromatography.

Procedure D—Oxidation of sulfide

A mixture of the sulfide (1 mmol) in 5 mL CH₂Cl₂ and 1.1 equivalents of MCPBA was stirred at room temperature for 5 hrs. The reaction was worked up by partitioning between water and ethyl acetate. The organic layer was separated and washed with brine then dried over sodium sulfate. The crude product was purified by chromatography.

Procedure E—Displacement of fluoride (FIG. 1E)

The arylfluoride (1 mmol) was added to 10 mL of an amine such as morphiline and mixture was heated to 80° C. and allowed to stir overnight. The reaction was worked up by partitioning between water and ethyl acetate. The organic layer was separated, washed with brine, and dried over sodium sulfate. The solvent was evaporated and the crude product was purified by chromatography.

The following tables provide the structures of compounds prepared according to the procedures above. Following the tables, specific reaction conditions are provided along with selected physical data for representative compounds of the present invention.

TABLE I

| R | Example |
|---|---|
| 2-Phenyl | 13 |
| 2-Piperidinyl | 24 |
| 2-(N-morpholino) | 25 |
| 2-Phenoxy | 16 |
| 4-Butyl | 20 |
| 4-Butoxy | 19 |

TABLE II

| B | Example |
|---|---|
| cyclopentyl | 11 |
| cyclohexyl | 6 |
| 2-furanyl | 1 |
| 2-(5-bromothienyl) | 2 |
| n-hexyl | 7 |
| benzyl | 4 |
| n-butyl | 8 |
| n-pentyl | 9 |
| phenethyl | 5 |

TABLE III

| Y and Z | Example |
|---|---|
| $C_6H_5$—, $C_6H_5$— | 15 |
| $C_6H_5S$—, H | 21 |
| H, Br | 12 |
| $C_6H_5CH_2$—, H | 17 |
| 2-thio-1-cyclohexyltetrazole, H | 23 |
| 4-$ClC_6H_5S$—, H | 22 |

TABLE IV

| W | Example |
|---|---|
| nonyl | 18 |
| 2-naphthyl | 14 |

The compounds in Table V below can be prepared using the methods provided in Examples 12 and 26, below.

TABLE V

R'
Phenyl
Benzyl
(2-Pyridyl)methyl
Phenethyl
2-(4-Pyridyl)ethyl
(3-Pyridyl)methyl
2-(2-Pyridyl)ethyl
Propyl
Cyclohexylmethyl
1-(1-ethynyl)cyclohexyl
2-Thiazolinyl
3-(1-Benzyl)pyrrolidinyl
4-(1-Phenethyl)piperazinyl
1-(5-Dimethylamino)pentyl
4-(1-Benzyl)piperazinyl
1-(3-Propyl)azepinyl
2-Oxazolinyl

EXAMPLE 1

N-cycloheptyl-4-[N-methyl-N-[(E)-3-(2-furanyl)-2-propenoyl]amino]benzenesulfonamide A mixture of 460 mg (1 mmole) of the phosphonate (VI) in 5 mL THF and 44 mg (1.1 mmol) sodium hydride was stirred under nitrogen until a clear yellow solution was obtained. To this solution was added 105 mg (1.1 mmol) of furan-2-carboxaldehyde and the reaction was stirred at room temperature for 2 hours then worked up by partitioning between 1N HCl and ethyl acetate (EtOAc). The crude orange solid was purified by chromatography to obtain 229 mg of the product as a white solid (57% yield). mp 152–5° C., TLC $R_f$=0.8 in 3% $CH_3OH$ in $CH_2Cl_2$ (DCM). $^1H$ NMR ($CDCl_3$, ppm): δ 8.0 (d, 2H, ArH); 7.5 (d, 1H, =CH); 7.4 (d, 2H, ArH), 7.38 (s, 1H, furan), 6.59 (s, 1H, furan), 6.48 (s, 1H, furan), 6.30 (s, 1H, =CH), 4.73 (d, 1H, NH), 3.51 (s, 3H, CH3), 1.6 (m, 13H, cycloheptyl) $^{13}C$ NMR ($CDCl_3$, ppm) 166.5, 1515.8, 147.8, 144.7, 140.5, 130, 128.9, 128.2, 116, 115, 112.8, 55.6, 37.9, 36.5, 28.5, 24. 403 ($MH^+$).

EXAMPLE 2
N-cycloheptyl-4-[N-methyl-N-[(E)-3-(2-(5-bromothienyl))-2-propenoyl]amino]benzene sulfonamide The title compound was prepared using the procedure of Example 1 using 5-bromothiophene-2-carboxaldehyde. mp: 153–155° C. TLC $R_f$=0.6 in 3% $CH_3OH/CH_2Cl_2$. $^1H$ NMR ($CDCl_3$, ppm): δ 8.5 (m, 1H), 8.0 (d, 2H), 7.8 (d, 1H), 7.7 (m, 1H), 7.5 (d, 2H), 7.4 (d, 1H), 7.0 (d, 1H), 4.7 (d, 1H), 3.51 (s, 3H), 1.6 (m, 13H); 498 ($MH^+$).

EXAMPLE 3
N-cycloheptyl-4-[N-methyl-N-[(E)-3-(2-(1-(4-chlorophenyl)pyrrolyl))-2-propenoyl]amino]-benzenesulfonamide The title compound was prepared using the procedure of Example 1 using N-(4-chlorophenyl)pyrrole-2-carboxaldehyde. mp: 172–175° C., TLC $R_f$=0.6 in 3% $CH_3OH/CH_2Cl_2$. $^1H$ NMR ($CDCl_3$): δ 8.5 (m, 1H), 8.0 (d, 2H), 7.8 (d, 1H), 7.7 (m, 1H), 7.5 (d, 2H), 7.4 (d, 1H), 7.0 (d, 1H), 4.7 (d, 1H), 3.51 (s, 3H), 1.6 (m, 13H);513 ($MH^+$).

EXAMPLE 4
N-cycloheptyl-4-[N-methyl-N-[(E)-3-(1-benzyl)-2-propenoyl]amino]benzene sulfonamide The title compound was prepared using the procedure of Example 1 using 2-phenylacetaldehyde. $^1H$-NMR ($CDCl_3$): δ 7.9 (d, 2H), 7.3 (m, 7H), 6.3 (bs, 2H), 4.8 (d, 2H), 3.4 (m, 4H), 3.0 (bs, 2H), 1.8 (m, 12H); $^{13}C$-NMR ($CDCl_3$): δ 147.9, 137.3, 133.6, 129.1, 129.1, 128.1, 126.8, 123.4, 55.6, 39.2, 38.1, 36.5, 28.5, 24.1; oil; TLC $R_f$ 0.51 in 50% EtOAc/Hexane; 427 ($MH^+$).

EXAMPLE 5
N-cycloheptyl-4-[N-methyl-N-[(E)-3-(1-phenethyl)-2-propenoyl]amino]benzene sulfonamide The title compound was prepared using the procedure of Example 1 using 3-phenylpropionaldehyde. $^1H$ NMR ($CDCl_3$): δ 7.9 (d, 2H), 7.3 (m, 5H), 7.1 (d, 2H), 7.0 (dt, 1H), 5.8 (d, 1H), 4.5 (d, 1H), 3.5 (m, 1H), 3.4 (s, 3H), 2.7 (t, 2H), 2.4 (q, 2H), 1.8 (m, 2H), 1.5 (m, 10H); mp, 39–42° C.; TLC $R_f$=0.54 in 5% $MeOH/CH_2Cl_2$; 441 ($MH^+$)

EXAMPLE 6
N-cycloheptyl-4-[N-methyl-N-[(E)-3-(1-cyclohexyl)-2-propenoyl]amino]benzene sulfonamide The title compound was prepared using the procedure of Example 1 using cyclohexane carboxaldehyde. mp: 129° C., $^1H$-NMR (CDCl3): δ 7.9 (d, 2H), 7.3 (d, 2H), 6.9 (dd, 1H), 5.7 (d, 1H), 4.7 (d, 1H), 3.4 (m, 1H), 3.3 (s, 3H), 1.5 (m, 24H); TLC $R_F$=0.54 in 10% $MeOH/CH_2Cl_2$; 419 ($MH^+$).

EXAMPLE 7
N-cycloheptyl-4-[N-methyl-N-[(E)-3-(1-hexyl)-2-propenoyl]amino]benzene sulfonamide The title compound was prepared using the procedure of Example 1 using 1-heptanal. $^1H$ NMR ($CDCl_3$): δ 7.9 (d, 2H), 7.3 (d, 2H), 7.0 (m, 1H), 5.8 (d, 2H), 4.8 (d, 1H), 3.4 (s, 4H), 2.1 (q, 2H), 1.8 (m, 2H), 1.4 (m, 15H), 0.8 (t, 3H). $^{13}C$ NMR ($CDCl_3$): δ 166.7, 148.3, 147.9, 140.4, 128.8, 128.1, 121.4, 121, 56.5, 37.8, 36.4, 32.9, 29.4, 28.7, 28.4, 24.1, 23.1, 14.6; oil; TLC $R_f$=0.5 in 40% EtOAc/Hexane; 427 ($MH^+$).

EXAMPLE 8
N-cycloheptyl-4-[N-methyl-N-[(E)-3-(1-butyl)-2-propenoyl]amino]benzene sulfonamide The title compound was prepared using the procedure of Example 1 using 1-pentanal. $^1H$ NMR ($CDCl_3$): δ 7.9 (d, 2H), 7.3 (d, 2H), 7.0 (dt, 1H), 5.7 (d, 1H), 4.8 (d, 1H), 3.5 (m, 1H), 3.4 (s, 1H), 2.1 (q, 2H), 1.5 (m, 12H), 0.8 (t, 3H). $^{13}C$ NMR ($CDCl_3$): δ 166.6, 148.2, 147.9, 140.4, 128.4, 128.1, 121.5, 55.6, 37.8, 36.5, 32.6, 30.8, 28.5, 24.1, 22.8, 14.3; mp 114° C.; TLC $R_f$=0.3 in 30% EtOAc/Hexane; 393 ($MH^+$).

EXAMPLE 9
N-cycloheptyl-4-[N-methyl-N-[(E)-3-(1-pentyl)-2-propenoyl]amino]benzene sulfonamide The title compound was prepared using the procedure of Example 1 using 1-hexanal. mp: 78° C., $^1H$-NMR ($CDCl_3$): δ 7.9 (d, 2H), 7.3 (d, 2H), 7.0 (dt, 1H), 5.6 (d, 1H), 4.8 (d, 1H), 3.4 (bs, 4H), 2.1 (m, 2H), 1.5 (m, 19H), 0.8 (m, 3H). $^{13}C$ NMR ($CDCl_3$): δ 148.2, 147.9, 128.8, 128.1, 121.4, 55.6, 37.8, 36.5, 32.8, 31.9, 28.5, 24.1, 22.9, 14.6; TLC $R_f$=0.34 in 40% EtOAc/Hexane; 407 ($MH^+$).

EXAMPLE 10
N-cycloheptyl-4-[N-methyl-N-[(E)-3-(1-cinnamyl)-2-propenoyl]amino]benzene sulfonamide The title compound was prepared using the procedure of Example 1 using cinnamaldehyde. mp: 153–155, $^1H$-NMR ($CDCl_3$): δ 8.0 (d, 2H), 7.5 (m, 8H), 7.0 (d, 1H), 6.8 (m, 1H), 6.0 (d, 1H), 4.7 (m, 1H), 3.4 (m, 1H), 3.3 (s, 3H), 2.0 (m, 3H), 1.6 (m, 12H); TLC $R_f$=0.59 in 3% $MeOH/CH_2Cl_2$; 439 ($MH^+$).

EXAMPLE 11
N-cycloheptyl-4-[N-methyl-N-[(E)-3-(1-cyclopentyl)-2-propenoyl]amino]benzene The title compound was prepared using the procedure of Example 1 using cyclopentane carboxaldehyde. mp: 103–105° C., $^1H$-NMR ($CDCl_3$): δ 7.9 (d, 2H), 7.3 (d, 2H), 6.9 (m, 1H), 5.7 (d, 1H), 4.5 (m, 1H), 3.4 (m, 1H), 3.3 (s, 3H), 2.5 (m, 1H), 1.6 (m, 20H); TLC $R_f$=0.82 in 3% $MeOH/CH_2Cl_2$; 405 ($MH^+$).

EXAMPLE 12
N-cycloheptyl-4-[N-methyl-N-bromoacetylamino]benzene sulfonamide

A mixture of 1 g (3.2 mmol) of the aniline (II) and 0.5 mL (3.5 mmol) of triethylamine in 10 mL of $CH_2Cl_2$ was stirred at 0° C. Bromoacetyl bromide (1.3 g, 6.3 mmol) was added slowly to this mixture. The reaction was allowed to stir at room temperature for 4 hrs then worked up by partitioning between water and ethyl acetate. The organic layer was separated, washed with brine and dried over sodium sulfate to give a crude brown oil (1.1 g). The crude mixture was purified by chromatography (200 mg) to afford 150 mg of an off-white powder. TLC $R_f$=0.4 by 50% EtOAc/Hexane; $^1H$ NMR (CDC13, ppm) 8.0 (d, 2H, ArH); 7.4 (d, 2H, ArH), 4.5 (m, 1H, NH), 3.7 (bs, 2H, CH2) 3.4 (s, 3H, NCH3), 1.4 (m, 1314, cycloheptyl); $^{13}C$-NMR ($CDCl_3$): 129.6, 111.9, 55.1, 36.5, 30.73, 28.5, 24.12; 404 ($MH^+$); mp=90° C.

EXAMPLE 13
N-cycloheptyl-4-[N-methyl-N-(1-2-phenyl)benzoyl)amino] benzene sulfonamide The procedure of Example 12 using 2-biphenyl-carbonylchloride. $^1H$ NMR ($CDCl_3$): δ 7.6 (s, 1H), 7.3 (m, 8H), 7.0 (m, 3H), 6.8 (m 2H), 6.1 (d, 1H), 4.4 (m, 1H), 3.2 (m, 4H), 1.6 (m, 12H); mp 142° C.; TLC $R_f$=0.45 in 50% EtOAc/Hexane; 463 ($MH^+$).

EXAMPLE 14
N-cycloheptyl-4-[N-methyl-N-(2-naphtoyl)amino]benzene sulfonamide

The procedure of Example 12 using 2-naphthoyl chloride. $^1$H NMR (CDCl$_3$): δ 8.0 (d, 2H), 7.8 (m, 2H), 7.7 (m, 2H), 7.1 (m, 2H), 4.6 (d, 1H), 3.4 (m, 4H), 1.6 (m, 12H); $^{13}$C NMR (CDCl$_3$): δ 163, 142, 124, 123.2, 122.6, 121.8, 121.4, 50.5, 31.4, 23.3, 18.9; mp 60° C.; TLC R$_f$=0.5 in 50% EtOAc/Hexane; 437 (MH$^+$).

EXAMPLE 15
N-cycloheptyl-4-[N-methyl-N-(1-(2-phenyl)phenylacetyl)amino]benzene sulfonamide The procedure of Example 12 using 2,2'-diphenylacetyl chloride. $^1$H NMR (CDCl$_3$): δ 8.0 (d, 2H), 7.8 (m, 2H), 7.7 (m, 4H), 7.1 (m, 6H), 4.6 (d, 1H), 3.4 (m, 4H), 1.6 (m, 12H). $^{13}$C NMR (CDCl$_3$): δ 147.9, 139.9, 129.3, 129.14, 129.1, 128.9, 128.8, 127.8, 55.6, 36.5, 28.5, 24.1; mp 65° C.; TLC R$_f$=0.75 in 50% EtOAc/Hexane; 477 (MH$^+$).

EXAMPLE 16
N-cycloheptyl-4-[N-methyl-N-(1-(2-phenoxy)benzoyl)amino]benzene sulfonamide The procedure of Example 12 using 2-phenoxy-1-benzoylchloride. $^1$H NMR (CDCl$_3$): δ 7.7 (d, 2H), 7.4 (d, 1H), 7.3 (m, 7H), 6.7 (d, 1H), 4.5 (d, 1H), 3.5 (s, 3H), 3.3 (m, 1H), 1.5 (m, 12H); $^{13}$C NMR (CDCl$_3$): δ 153.5, 139.3, 131.5, 130.4, 130.1, 128, 127.4, 124.6, 119.8, 55.4, 36.4, 28.5, 24; mp, 70–73° C.; TLC R$_f$=0.5 in 10% MeOH/CH$_2$Cl$_2$; 479 (MH$^+$).

EXAMPLE 17
N-cycloheptyl-4-[N-methyl-N-) (1)amino]benzene sulfonamide

The procedure of Example 12 using 3-phenylpropionyl chloride. $^1$H NMR (CDCl$_3$): δ 7.8 (d, 2H), 7.3 (d, 2H), 7.2 (m, 5H), 4.6 (d, 1H), 3.4 (m, 1H), 3.3 (s, 3H), 2.9 (t, 2H), 2.4 (m, 2H), 1.8 (m, 2H), 1.5 (m, 12H); mp 85° C.; TLC R$_f$=0.5 in 50% EtOAc/Hexane; 415 (MH$^+$).

EXAMPLE 18
N-cycloheptyl-4-[4[N-methyl-N-(1-nonyl)amino]benzene sulfonamide

The procedure of Example 12 using 1-nonyl chloride. $^1$H NMR (CDCl$_3$): δ 8.0 (d, 2H), 7.4 (d, 2H), 4.8 (m, 1H), 3.5 (m, 1H), 3.3 (s, 3H), 2.2 (bs, 2H), 2.0 (bs, 2H), 1.7 (m, 12H), 1.3 (s, 10H), 0.8 (t, 3H); $^{13}$C NMR (CDCl$_3$): δ 166.7, 148.2, 128.3, 128.1, 55.5, 37.8, 36.5, 32.6, 30.8, 28.5, 24.1, 22.8, 14.3; oil; TLC R$_f$=0.64 in 3% MeOH/CH$_2$Cl$_2$; 423 (MH$^+$).

EXAMPLE 19
N-cycloheptyl-4-[N-methyl-N-(1-(4-butoxybenzoyl))amino]benzene sulfonamide The procedure of Example 12 using 4-butoxybenzoyl chloride. $^1$H NMR (CDCl$_3$): δ 7.9 (d, 2H), 7.2 (d, 2H), 7.1 (d, 2H), 6.7 (d, 2H), 4.4 (d, 1H), 4.0 (t,2H), 3.5 (s, 3H), 3.4 (s, 1H), 1.8 (m, 3H), 1.4 (m, 16H), 0.8 (t, 3H); mp, 38–41° C.; TLC R$_f$=0.59 in 3% MeOH/CH$_2$Cl$_2$; 459 (MH$^+$).

EXAMPLE 20
N-cycloheptyl-4-[N-methyl-N-(1-(4-butylbenzoyl))amino]benzene sulfonamide The procedure of Example 12 using 4-butylbenzoyl chloride. $^1$H NMR (CDCl$_3$): δ 7.8 (d, 2H), 7.3 (d, 2H), 7.2 (d, 2H), 7.0 (d, 2H), 4.6 (m, 1H), 3.4 (s, 3H), 3.4 (m, 1H), 2.5 (t, 2H), 1.5 (m, 18H), 0.8 (t, 3H); mp 36–39° C.; TLC R$_f$=0.67 in 3% MeOH/CH$_2$Cl$_2$; 443 (MH$^+$).

EXAMPLE 21
N-cycloheptyl-4-[N-methyl-N-(1-(2-thiophenyl)acetyl)amino]benzene sulfonamide To 404 mg (1 mmol) of the bromide (V) in 5 mL of methylene chloride was added 320 mg (1.1 mmol) of ZnI2 followed by 160 mg (1.5 mmol) of thiophenol. Reaction was stirred overnight at room temperature under nitrogen. Worked up reaction by partitioning between water and ethyl acetate. The organic layer dried over sodium sulfate, the solvent removed and residue subjected to purification on a preparative plate (Uniplate 2000 microns) using 10% MeOH/CH2Cl2 to afford 300 mg (60% yield) of a waxy solid. mp: 68° C.; TLC R$_f$=0.33 in 30% EtOAc/Hexane. $^1$H NMR (CDC13, ppm): δ 7.9 (d, 2H), 7.3 (d, 2H), 4.6 (d, 1H), 3.6 (s, 2H), 3.4 (m, 4H), 1.6 (m, 13H); 433 (MH$^+$).

EXAMPLE 22
N-cycloheptyl-4-[N-methyl-N-(1-(2-(4-chloro)thiophenyl)-acetyl)amino]benzene sulfonamide The title compound was prepared using the procedure of Example 21 using 4-chlorothiophenol. $^1$H NMR (CDCl$_3$): δ 8.5 (m, 1H), 8.0 (d, 2H), 7.8 (d, 1H), 7.7 (m, 1H), 7.5 (d, 2H), 7.4 (d, 1H), 7.0 (d, 1H), 4.7 (d, 1H), 3.51 (s, 3H), 1.6 (m, 13H); IR (nujol mull): cm$^{-1}$ 3273, 2928, 2857, 1645, 1593, 1435, 1159; Mass spec (MH$^+$) 467; mp 115–118° C.; TLC R$_f$=0.6 in 3% MeOH/CH$_2$Cl$_2$.

EXAMPLE 23
N-cycloheptyl-4-[N-methyl-N-(1-(2-(2-thio-1-cyclohexyl) tetrazoyl)-acetyl)amino]benzene sulfonamide The title compound was prepared using the procedure of Example 21 using 2-thio-1-cyclohexyl-tetrazole. $^1$H NMR (CDCl$_3$): δ 8.0 (d, 2H), 7.5 (d, 2H), 4.5 (m, 1H), 4.2 (m, 1H), 4.2 (m, 1H), 3.5 (bs, 1H), 3.4 (s, 3H), 2.0 (m, 10H), 1.5 (m, 12H). Mass Spec. (MH$^+$) 507; mp 60–65° C.; TLC R$_f$=0.3 in 3% MeOH/CH$_2$Cl$_2$.

EXAMPLE 24
N-cycloheptyl-4-[N-methyl-N-(1-(2-piperidine)-benzoyl)amino]benzene sulfonamide To a mixture of 403 mg (1 mmol) of N-cycloheptyl-4-[N-methyl-N-(1-(2-fluorobenzoyl)amino]benzene sulfonamide (prepared according to procedure A above using 2-fluorobenzoyl chloride), was added 60 mL of piperidine and the mixture refluxed overnight. The reaction stopped by removal of the piperidine on a rotary evaporator, the residue is subjected to purification on a preparative plate (Uniplate 2000 microns) using 10% MeOH/CH$_2$Cl$_2$ to afford 400 mg (80% yield) of a white solid. mp 74° C.; TLC R$_f$=0.5 in 30% EtOAc/Hexane; $^1$H NMR (CDC13, ppm): δ 7.5 (m, 8H), 4.6 (m, IH), 3.5 (m, 3H), 3.2 (m, 2H), 2.9 (m, 2H) 1.6 (m, 17H); 470 (MH$^+$).

EXAMPLE 25
N-cycloheptyl-4-[N-methyl-N-(1-(2-morpholino)-benzoyl)amino]benzene sulfonamide The title compound was prepared using the procedure of Example 24 using morpholine. $^1$H NMR (CDCl$_3$): δ 7.5 (m, 8H), 4.6 (m, 1H), 3.8 (m, 4H), 3.3 (m, 6H), 1.6 (m, 13H); mp 131° C.; TLC R$_f$=0.2 in 3% MeOH/CH$_2$Cl$_2$; 471 (MH$^+$).

EXAMPLE 26
Step 1: 4-(N-Acetyl-N-methylamino)benzene sulfonyl chloride

A solution of ice cold chlorosulfonic acid (90 mL) is slowly added 39.8 g (267 mmol) of N-methyl acetanilide. After addition complete the reaction is heated to 70° C. for 2 hours then cooled to room temperature. The slurry is slowly added into an ice/water mixture with rapid stirring. The white solid formed is filtered and washed with water and hexanes to give 50.1 g (80% yield) of the sulfonyl chloride. mp 122–6° C., TLC $R_f$=0.17 in 50% ethyl acetate in hexane. $^1$H NMR (CDCl$_3$, ppm): δ 8.0 (d, 2H, ArH), 7.49 (m, 3H), 7.3 (m, 2H, p-chlorophenyl), 7.2 (d, 2H, ArH), 6.8 (s, 1H, pyrrole), 6.5 (s, 1H, pyrrole), 6.3 (s, 1H, pyrrole), 6.0 (d, 1H,=CH), 4.6 (d, 1H, NH), 3.50 (s, 3H, N-CH3), 1.6 (m, 13H, cycloheptyl).

Step 2: N-Phenyl-4-[N-methyl-amino]benzene sulfonamide

A mixture of 50.1 g (212 mmol) of sulfonyl chloride and 24 g (212 mmol) of aniline and 61 g of sodium acetate were stirred in ethanol at 0° C. under an atmosphere of nitrogen. Worked up by partitioning between water and ethyl acetate, the organic layer was separated, washed with brine and dried over sodium sulfate to give a colorless oil. The oil was dissolved in ethanol, NaOH (4 g) was added and the solution was refluxed for 16 hours. The reaction was cooled to 0° C. and pH was adjusted to 8.0. The white solid was filtered, washed with hexane and dried to yield 39.5 g of product (71% yield). mp 113–114° C.; TLC $R_f$=0.42 in 50% EtOAc/Hexane; $^1$H NMR (CDCl$_3$, ppm) δ 7.67 (d, 2H, ArH); 6.56 (d, 2H, ArH); 3.3 (m, 1H); 2.9 (d, 3H,NCH3) 1.8 (m, 2H); 1.4 (m, 11H, cycloheptyl). $^{13}$C-NMR (CDCl$_3$): 129.6, 111.9, 55.1, 36.5, 30.73, 28.5, 24.12. MS: 283 (MH$^+$).

Step 3: N-phenyl-4-[N-methyl-N-(1-nonyl)amino]benzene sulfonamide

The procedure of Example 17 was carried out using nonyl chloride and the product from Step 2 above. mp: 113–116° C.; TLC $R_f$=0.38 in MeOH/CH$_2$Cl$_2$; $^1$H NMR (CDC13, ppm) δ 7.9 (d, 2H), 7.6 (d, 5H), 7.3 (d, 2H), 7.0 (bs, 1H), 3.0 (s, 3H), 2.0 (t, 2H), 1.4 (m, 12H), 0.9 (t, 3 H)

EXAMPLE 27

N-(N-phenyl-4-aminopiperidine)-4-[N-methyl-N-(1-nonyl)amino]benzene sulfonamide

The title compound was prepared using the procedure of Example 26 using N-phenyl-4-aminopiperidine. $^1$H NMR (CDCl$_3$): δ 8.0 (d, 2H), 7.3 (d, 7H), 7.3 (d, 2H), 3.7 (bs, 2H), 3.4 (s, 3H), 2.9 (m, 2H), 2.2 (m, 4H), 1.8 (m, 4H), 1.2 (m, 12H), 0.9 (t, 3H); oil; TLC $R_f$=0.44 in 3% MeOH/CH$_2$Cl$_2$; 486 (MH$^+$).

EXAMPLE 28

The compounds of the present invention were assayed for cPLA2 activity using cPLA2 enzyme from the cytosolic extraction of U937 cells.

Cytosolic extraction of U937 cells (all procedures carried out on ice)

U937 cells were harvested and spun for five minutes at 1000 g and washed at least three times in extraction buffer (140 mM NaCl, 5 mM KCl, 2 mM EDTA, 25 mM Tris, pH 7.4 solution). The cells were then suspended in buffer (1×10$^8$ cells/mL) and protease inhibitors were added to achieve the following concentrations: 100 μM leupeptin, 50 μM pepstatin, and 1 mM PMSF. The cells were placed in a N$_2$ cavitation bomb and put under pressure to 600 psi for 20 minutes in a cold room. The suspension was released and collected, then spun at 100,000 g for 60 minutes at 4° C. The supernatent was collected, filtered through a 0.22 μM filter, diluted to 50% with glycerol, aliquoted and stored at −20° C.

cPLA2 Enzyme Assay using U937 Cytosolic Extract as Enzyme Source

Materials and Chemicals:

Phosphatidylcholine L-α-1-palmitoyl-2-arachidonyl-1 [$^{14}$C] was obtained from New England Nuclear (NEC-765). 1,2-dioleyl-glycerol was obtained from Avanti Polar Lipids (800811 in CHCl$_3$). The substrate buffer was 150 mM NaCl and 50 mM HEPES at pH 7.5. 100 mg/mL BSA (ICN 823234) was made up in water. The assay buffer was 150 mM NaCl, 50 mM HEPES at pH 7.5, 1 mM CaCl$_2$ and 1 mM 2-ME. Dole's Reagent: 2-propanol/heptane/0.5 M H$_2$SO$_4$ (40:10:1) containing 10 μg/mL stearic acid. Silica gel was 100–200 μm (70–150 mesh) (obtained from Universal Scientific Inc. 02760). Ready Safe® scintillation cocktail, 96-well deep well plates (No. 267007) and foil seals for microtiler plates (No. 538619) were all obtained from Beckman Scientific. Nunc microtiter plates were also used along with 7 mL size scintillation vials and tops.

Instruments:

Hamilton Microlab AT Plus was used with a 37° C. incubator and a Beckman scintillation counter.

Hamilton At Plus Programs:

The Hamilton Microlab AT Plus was used to dilute compounds in DMSO from a 80× highest dose 1:5 dilutions for a total of 5 concentrations (80× of each dose).

The Hamilton Microlab AT Plus runs the PLA2 assay by pipetting the DMSO dilutions into diluted extract in assay buffer (1–3 μL/well—determined by lot of extraction) into a plate for a preincubation of 20 min at 37° C. This mixture is then pipetted into the radiolabeled liposomes (substrate) starting the reaction. The program also stops the reactions, does the heptane extractions, and transfers it to the silica gel.

Procedure:

Preparation of Substrate:

1. Pipette 23 μL of the radiolabeled substrate into a glass test tube. Add 3.1 μL of the 1,2-dioleylglycerol (using a Hamilton syringe pipette). Dry gently under a nitrogen or argon stream.
2. Bring up in 1 mL of substrate buffer. Sonicate with Branson sonifier for 2 min. at 50% at max setting.
3. Add 40 μL of 100 mg/mL BSA solution. Keep on ice or at 4° C.

Preparation of Compounds:

1. In a 96-well Nunc Polysorp plate pipette 80 μL DMSO into B1, B7, C$_1$, C7, D1, D7 and into each of these wells, add 20 μL of a 10 mM stock solution of 6 compounds in DMSO.
2. The Hamilton Microlab dilutes each compound in DMSO ⅕ in serial dilutions to yield a total of five concentrations.
3. The next program dilutes the DMSO serial dilutions into Assay buffer containing U937 extract (5 μL compound+ 295 μL diluted enzyme). Then plate is placed in 37° C. for 20 min preincubation. In the same plate, controls with assay buffer alone are added and also U937 extract diluted in assay buffer containing 50 mM EGTA with no calcium added.
4. During preincubation of enzyme with compound, prewarm a deepwell plate at 37° C. Pipette 10 μL/well of substrate mixture before preincubation time is up.

Reaction Begins:

1. When preincubation time is complete, Hamilton mixes and adds 30 μL of each compound/extract dilution to wells with substrate in each well. Reaction starts. Place plate back in 37° C.
2. Incubate 37° C. for 15 min.
3. Restart program. Dole's reagent will be added to stop reactions (400 μL). Next Heptane will be added (240 μL) and then H$_2$O (200 μL).
4. Prepare corresponding deepwell plate for each reaction tube with 60 mg silica gel with 200 μL heptane. Hamilton will pipette 280 μL of top layer (Heptane phase) from first plate to silica gel plate.

5. Seal plate with foil seal tops. Mix vigorously on microtiter plate shaker. Centifuge 1000 g for 1 min. Hamilton will transfer 400 μL from each well to 7 mL scintillation vials.
6. Add 4 mL Ready Safe Beckman scintillation cocktail. Count.

EXAMPLE 29

Assays for evaluation of arylsulfonamides
Primary Rat Cortical or Hippocampal Neurons:

Cultures of rat cortical neurons were established from 18 day rat fetuses. Cortical tissue was dissociated by incubation in a trypsin/EDTA solution (0.05% trypsin+0.53 mM EDTA in HBSS; Gibco) for 20 minutes at 37° C. The trypsin was then inactivated by resuspending the cells in serum-containing medium (DMEM/FBS): Dulbecco's Modified Eagle's Medium (DMEM) containing 4.5 g/L glucose, 1 mM sodium pyruvate, 1 mM glutamine, 100 Units/mL penicillin, 100 μg/mL streptomycin, and supplemented with 10% heat-inactivated fetal bovine serum (Gibco). Cells were then pelleted by centrifugation and resuspended in a chemically-defined medium (DMEM/B27): DMEM containing B27 supplement (Gibco) in place of FBS. Polyethyleneimine (PEI)-coated 6.4-mm (96-well) dishes were rinsed once with DMEM/FBS, and then seeded at 0.75–1.25×10$^5$ cells per well in 0.1 mL DMEM/B27. Cultures were maintained in a H$_2$O)-saturated incubator with an atmosphere of 90% air/10% CO$_2$ at 37° C. Cell viability was visually assessed by phase contrast microscopy and quantified by measuring the reduction of alamarBlue™ (Alamar Biosciences, Inc.) as described below. Serum replacement with B27 supplement yields nearly pure neuronal cultures as judged by immunocytochemistry for glial fibrillary acidic protein and neuron-specific enolase (Brewer et al. (1993), *J. Neurosci. Res.* 35(5):567–576.

Primary Human Cortical or Hippocampal Neurons:

Cultures of human cortical neurons were prepared using a modification of the procedure described in P. Seubert et al. (1992), *Nature* 359:325–327. Cortical tissue was dissociated by incubation in a trypsin/EDTA solution (0.05% trypsin+ 0.53 mM EDTA in HBSS; Gibco) for 20 minutes at 37° C. The trypsin was then inactivated by resuspending the cells in serum-containing medium (MEM/FBS): Modified Eagle's Medium (MEM) containing 1% glucose, 1 mM sodium pyruvate, 1 mM glutamine, and supplemented with 10% fetal bovine serum (Gibco). Cells were then pelleted by centrifugation and resuspended in a chemically-defined medium (MEM/B27): MEM containing B27 supplement (Gibco) in place of FBS. Polyethyleneimine (PEI)-coated 6.4-mm (96-well) dishes were rinsed once with MEM/FBS, and then seeded at 0.75–1.25×10$^5$ cells per well in 0.1 mL MEM/B27. Cultures were maintained in a H$_2$O-saturated incubator with an atmosphere of 95% air/5% CO$_2$ at 37° C. The culture medium was exchanged twice weekly.

Primary Human Cortical or Hippocampal Astrocytes and Microglia:

Cultures of human cortical astrocytes and microglia were prepared using a modification of the procedure described for cortical neurons. Cortical tissue from fetuses of 16 to 20 weeks of gestation was washed 3 times in Ca$^{2+}$/Mg$^{2+}$ free Hanks balanced salt solution (CMF HBSS) and then dissociated by repeated pipetting. The solution was brought to a final volume of 80 mL CMF HBSS for approximately 10 mL of tissue. DNase (Sigma) was added to a final concentration of 0.05 mg/mL. 20 mL of the solution was passed through one 100 μm nylon cell strained (Falcon). The cells were then centrifuged for 5 minutes at 200×G in an IEC Clinical Centrifuge and resuspended in a trypsin/EDTA solution (0.05% trypsin+0.53 mM EDTA in HBSS; Gibco) and incubated for 20 minutes at 37° C. (10 mL of trypsin was added per 2–3 mL of tissue). The trypsin was then inactivated by adding (MEM/FBS): Modified Eagle's Medium (MEM) containing 1% glucose, 1 mM sodium pyruvate, 1 mM glutamine, and supplemented with 10% fetal bovine serum (JRH). After adding a final concentration of 0.05 mg/mL DNase the cells were resuspended and then pelleted by centrifugation and resuspended in MEM/FBS. 1.6×10$^8$ cells were seeded in a T-150 tissue culture flask coated with polyethyleneimine (PEI). (10% PEI (Sigma) was diluted 1:10 in H$_2$O, filtered through a 45 mm unit and then diluted into 150 mM sodium borate pH 8.5 at 1:100. The flasks were coated overnight at room temperature, washed two times in PBS and coated with 20 mL/flask of MEM/FBS at 37° C. for at least one hour prior to plating cells.) Cultures were maintained in a H$_2$O-saturated incubator with an atmosphere of 95% air/5% CO$_2$ at 37° C. The culture medium was changed one and four days after plating and the cultures were then left undisturbed for at least one week. After approximately two weeks in vitro, the flasks were gently shaken and floating microglia were collected and centrifuged for 5 minutes at 200×G in an IEC Clinical Centrifuge. The microglia were reseeded in 96 well tissue culture plates at a density of 5,000–40,000 cells/well in 125 μL in MEM/ FBS. Astrocyte cultures were prepared by multiple passaging of the established mixed brain cell cultures. Each T-150 was incubated for 3–4 minutes at 37° C. with a trypsin/ EDTA solution (see above). The trypsin was then inactivated by adding MEM/FBS. The cells were triturated and then pelleted by centrifugation and resuspended in MEM/FBS. The cells from one T-150 were seeded at a 1:30 to 1:5 dilution in T-150's not coated. Just prior to confluency the cells were repassaged by trypsinization as described above. This process was repeated until the cultures were >98% pure astrocytes.

Experimental Treatments and Analysis of Neuronal Survival:

Amyloid-β (Aβ) stock solutions were prepared as 1 mM stocks in sterile ddH$_2$O immediately prior to addition to cultures. Rat cortical neurons were exposed to Aβ by removing the culture medium and replacing it with DMEM/N2 or DMEM/B27 containing Aβ1-40. Human cortical neurons were exposed to Aβ by removing the culture medium and replacing it with MEM, MEM/N2, or MEM/B27 containing Aβ1-40. Cultures were maintained for 2–4 days before neuronal survival was quantified using alamarBlue™.

Neurotoxicity Assay using alamarBlue™:

The alamarBlue™ assay incorporated a proprietary fluorometric/colorimetric metabolic indicator (Alamar Biosciences, Inc.). Viable cells convert alamarBlue™ from an oxidized (non-fluorescent, blue) form to a reduced (fluorescent, red) form. Assays were performed by replacing the culture media with a 10% alamarBlue™ solution in DMEM (rat cortical cultures) or MEM (human cortical cultures). Reduction of alamarBlue™ was determined spectrofluorometrically using a Millipore Cytofluor 2350 Scanner (excitation, 560 mM; emission, 590 nm) and CytoCalc™ software (Millipore Corporation). Neuronal viability as assessed by alamarBlue™ was comparable to that obtained by measuring the fluorogenic probe calcein AM, the release of the cytoplasmic enzyme lactate dehydrogenase (LDH), or the reduction of the tetrazolium salt, 2,3-bis (2-methoxy-4-nitro-5-sulfophenyl)-2H-tetrazolium-5-carboxanilide (XTT).

Aβ Induces Cytokine Release in Microglia

Cultured microglial cells were treated with 50 μM of Aβ1-40 or vehicle only (Control). The levels of IL-1β and TNF-α released into the culture medium were determined by ELISA assay (R&D Systems) according to manufacturer's instructions. Aβ1-40 was found to stimulate the release of IL-1β and TNF-α. The effect of this stimulation could be reversed using compounds provided herein. In particular, certain compounds provided ≧35% inhibition at concentrations of ≦10 μM.

IL-1 Release in Human THP-1 Cells

Compounds of the present invention were evaluated for their ability to inhibit IL-1 release from human THP-1 cells using the methods described in Lorton, et al., *J. Neuroimmunology* 67:21–29 (1996) with the modification of using IFN-γ in place of LPS as a co-stimulent. A number of compounds were found to provide ≧35% inhibition at concentrations of ≦10 μM.

NGF Deprivation-Induced Apoptosis

Sympathetic neurons in culture die by apoptosis when deprived of NGF (Martin et al. (1988), J. Cell Biol. 106:829–844). Rat sympathetic neurons can be evaluated when deprived of NGF in the presence of compounds described herein. Neuronal viability is assessed 24–30 hours later by their appearance and using phase-contrast light microscopy and compared to neurons maintained in the presence of 100 ng/mL NGF. Neurons maintained in the presence of NGF typically have a soma that is smooth and round to oval in shape, and possess neurites with a relative uniform diameter and smooth appearance. Neurons deprived of NGF are characterized by neurite fragmentation, a shrunken and collapsed soma, and cell lysis. Neurons deprived of NGF in the presence of the compounds described herein will typically exhibit intact neurites and a smooth to shrunken soma.

VII. Conclusion

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A compound having the formula:

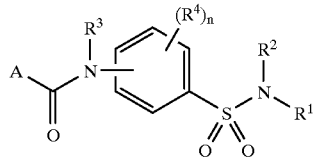

wherein

A represents a $C_4$–$C_{10}$ alkyl group, an aryl group, an arylalkyl group, radicals selected from the group consisting of —CH=CH—B, —S—B, and —NH—B, or radicals of formula —$CH_2$—X,
wherein B represents a non-aromatic $C_3$–$C_8$ carbocycle, a $C_3$–$C_8$ alkyl group, or a heterocycle, each of which is optionally substituted with one or more members independently selected from the group consisting of a halogen atom, a $C_1$–$C_4$ alkyl group, a $C_1$–$C_4$ alkoxy group, cyano, nitro, a heterocycle, an aryl group and an aryloxy group, and X is a member selected from the group consisting of a halogen atom, —S—aryl, —S—heterocycle, and —$PO_3R_2$ wherein each R is independently selected from the group consisting of a hydrogen atom and $C_1$–$C_3$ alkyl;

$R^1$ and $R^2$ each independently represent a hydrogen atom, a lower alkyl group, an unsubstituted cycloalkyl group, a cycloalkyl group substituted with a lower alkyl or halogen, a group represented by the formula: —$(CH_2)_q$—A' wherein q is an integer of 1 to 4, and A' is a member selected from the group consisting of a hydroxyl group, a group represented by the formula:

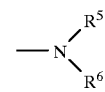

wherein $R^5$ and $R^6$ each independently represent a hydrogen atom, a lower alkyl group, or a group represented by the formula:

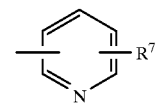

wherein $R^7$ represents a hydrogen atom, a lower alkyl group, or a group represented by the formula:

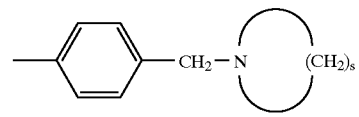

wherein s is an integer of 2 to 5, or
a cycloalkyl group condensed with an aromatic ring, a bicycloalkyl, or tricycloalkyl, said bicycloalkyl or tricycloalkyl being an aliphatic saturated hydrocarbon group made of two or three rings, respectively, with at least two carbon atoms being common to each ring, or an azabicycloalkyl group which is a bicycloalkyl group as described above in which one carbon atom is replaced by a nitrogen atom or a group represented by the formula:

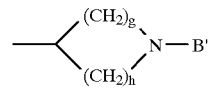

wherein g and h are each an integer of 1 to 4, and B' stands for a lower alkyl group, an arylalkyl group, an arylalkyl group substituted by lower alkyl, halogen or a lower alkoxy group, or a pyridylalkyl group, or a pyridylalkyl group substituted with a lower alkyl group, a halogen or a lower alkoxy group;

$R^3$ represents a hydrogen atom, a lower alkyl group, or a $C_3$–$C_8$ cycloalkyl group;

$R^4$ represents a hydrogen atom, a lower alkyl group, a lower alkoxy group or a halogen atom; wherein
n is an integer of 1 to 4, or, alternatively, n is 2, and the two $R^4$ groups may form a cyclohexenyl or phenyl ring together with two adjacent carbon atoms constituting the benzene ring;

wherein
an aryl group is a member selected from the group consisting of a phenyl ring and a naphthyl ring, wherein said aryl group is unsubstituted or substituted with at least one member selected from the group consisting of a halogen, an alkyl, an alkoxy, an alkylthio, an trifluoromethyl, an acyloxy, a hydroxy, a mercapto, a carboxy, an aryloxy, an arylalkyl, a heteroaryl, a heterocycle and an amino group;
wherein $C_3$–$C_8$ carbocycle is a member of the group consisting of a nonaromatic cyclic carbon compound having between 3 to 8 carbons in said ring and optionally having at least one site of unsaturation;
wherein
a heterocycle group is a member selected from the group consisting of a single ring or multiple condensed rings, said heterocycle group having between four to ten total ring atoms wherein between one and four of said total ring atoms are heteroatoms selected from the group consisting of N, O, and S wherein said heterocycle group is optionally unsubstituted or substituted with at least one member selected from the group consisting of halogen, alkyl, cycloalkyl, alkoxy, alkylthio, trifluoromethyl, acyloxy, hydroxy, mercapto, carboxy, aryloxy, aryl, arylalkyl, and heteroaryl; and pharmacologically acceptable salts thereof.

2. A compound in accordance with claim 1, wherein A is —CH═CH—B.

3. A compound in accordance with claim 2, wherein B is $C_3$–$C_8$ alkyl, $R^3$ is methyl and $R^1$ is cycloheptyl.

4. A compound in accordance with claim 2, wherein B is arylalkyl, $R^3$ is methyl and $R^1$ is cycloheptyl.

5. A compound in accordance with claim 2, wherein B is a carbocycle, $R^3$ is methyl and $R^1$ is cycloheptyl.

6. A compound in accordance with claim 2, wherein B is a heterocycle, $R^3$ is methyl and $R^1$ is cycloheptyl.

7. A compound in accordance with claim 1, wherein A is aryl, $R^3$ is methyl and $R^1$ is cycloheptyl.

8. A compound in accordance with claim 1, wherein A is alkyl, $R^3$ is methyl and $R^1$ is cycloheptyl.

9. A compound in accordance with claim 1, wherein A is diphenylmethyl, $R^3$ is methyl and $R^1$ is cycloheptyl.

10. A compound in accordance with claim 1, wherein A is phenoxyphenyl, $R^3$ is methyl and $R^1$ is cycloheptyl.

11. A pharmaceutical composition for the treatment of neurodegenerative diseases, said composition comprising in unit dosage form a compound having the formula:

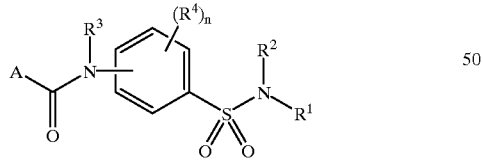

wherein
A represents a $C_4$–$C_{10}$ alkyl group, an aryl group, an arylalkyl group, radicals selected from the group consisting of —CH═CH—B, —S—B, and —NH—B, or radicals of formula —CH$_2$—X,
wherein B represents a non-aromatic $C_3$–$C_8$ carbocycle, a $C_3$–$C_8$ alkyl group, or a heterocycle, each of which is optionally substituted with one or more members independently selected from the group consisting of a halogen atom, a $C_1$–$C_4$ alkyl group, a $C_1$–$C_4$ alkoxy group, cyano, nitro, a heterocycle, an aryl group and an aryloxy group, and X is a member selected from the group consisting of a halogen atom, —S—aryl, —S—heterocycle, and —PO$_3$R$_2$ wherein each R is independently selected from the group consisting of a hydrogen atom and $C_1$–$C_3$ alkyl;

$R^1$ and $R^2$ each independently represent a hydrogen atom, a lower alkyl group, an unsubstituted cycloalkyl group, a cycloalkyl group substituted with a lower alkyl or halogen, a group represented by the formula: —(CH$_2$)$_q$—A' wherein q is an integer of 1 to 4, and A' is a member selected from the group consisting of a hydroxyl group, a group represented by the formula:

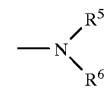

wherein $R^5$ and $R^6$ each independently represent a hydrogen atom, a lower alkyl group, or a group represented by the formula:

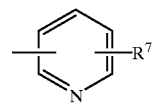

wherein $R^7$ represents a hydrogen atom, a lower alkyl group, or a group represented by the formula:

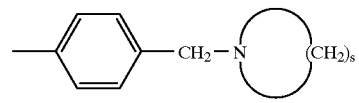

wherein s is an integer of 2 to 5, or
a cycloalkyl group condensed with an aromatic ring, a bicycloalkyl, or tricycloalkyl, said bicycloalkyl or tricycloalkyl being an aliphatic saturated hydrocarbon group made of two or three rings, respectively, with at least two carbon atoms being common to each ring, or an azabicycloalkyl group which is a bicycloalkyl group as described above in which one carbon atom is replaced by a nitrogen atom or a group represented by the formula:

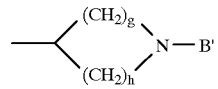

wherein g and h are each an integer of 1 to 4, and B' stands for a lower alkyl group, an arylalkyl group, an arylalkyl group substituted by lower alkyl, halogen or a lower alkoxy group, or a pyridylalkyl group, or a pyridylalkyl group substituted with a lower alkyl group, a halogen or a lower alkoxy group;

$R^3$ represents a hydrogen atom, a lower alkyl group, or a $C_3$–$C_8$ cycloalkyl group;

$R^4$ represents a hydrogen atom, a lower alkyl group, a lower alkoxy group or a halogen atom; wherein
n is an integer of 1 to 4, or, alternatively, n is 2, and the two $R^4$ groups may form a cyclohexenyl or phenyl ring together with two adjacent carbon atoms constituting the benzene ring;

wherein
an aryl group is a member selected from the group consisting of a phenyl ring and a naphthyl ring, wherein said aryl group is unsubstituted with at least one member selected from the group consisting of a halogen, an alkyl an alkoxy, an alkylthio, an trifluoromethyl, an acyloxy, a hydroxy, a mercapto, a carboxy, an aryloxy, an arylalkyl, a heteroaryl, a heterocycle and an amino group;
wherein
$C_3$–$C_8$, carbocycle is a member of the group consisting of a nonaromatic cyclic carbon compound having between 3 to 8 carbons in said ring and optionally having at least one site of unsaturated;
wherein
a heterocycle group is a member selected from the group consisting of a single ring or mutiple condensed rings, said heterocycle group having between four to ten total ring atoms wherein between one and four of said total ring atoms are heteroatoms selected from the group consisting of N, O, and S wherein said heterocycle group is optionally unsubstituted or substituted with at least one member selected from the group consisting of halogen ,alkyl, cycloalkyl alkoxy, alkylthio, trifluoromethyl, acyloxy, hydroxy, mercapto, carboxy aryloxy, aryl, arylalkyl, and heteroaryl; and any pharmacologically acceptable salts thereof in a pharmaceutically acceptable excipient.

12. A composition in accordance with claim 11, wherein A is a radical of formula —CH═CH—B.

13. A composition in accordance with claim 12, wherein B is alkyl, $R^3$ is methyl and $R^1$ is cycloheptyl.

14. A composition in accordance with claim 12, wherein B is arylalkyl, $R^3$ is methyl and $R^1$ is cycloheptyl.

15. A composition in accordance with claim 12, wherein B is a carbocycle, $R^3$ is methyl and $R^1$ is cycloheptyl.

16. A composition in accordance with claim 12, wherein B is a heterocycle, $R^3$ is methyl and $R^1$ is cycloheptyl.

17. A composition in accordance with claim 11, wherein A is aryl, $R^3$ is methyl and $R^1$ is cycloheptyl.

18. A composition in accordance with claim 11, wherein A is alkyl, $R^3$ is methyl and $R^1$ is cycloheptyl.

19. A composition in accordance with claim 11, wherein A is diphenylmethyl, $R^3$ is methyl and $R^1$ is cycloheptyl.

20. A composition in accordance with claim 11, wherein A is phenoxyphenyl, $R^3$ is methyl and $R^1$ is cycloheptyl.

21. A method for inhibiting neuronal degeneration in a host, comprising administering to said host an efficacious dose of a compound of the formula:

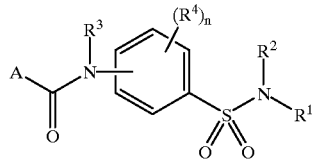

wherein
A represents a $C_4$–$C_{10}$ alkyl group, an aryl group, an arylalkyl group, radicals selected from the group consisting of —CH═CH—B, —S—B, and —NH—B, or radicals of formula —CH$_2$—X,
wherein B represents a non-aromatic $C_3$–$C_8$ carbocycle, a $C_3$–$C_8$ alkyl group, or a heterocycle, each of which is optionally substituted with one or more members independently selected from the group consisting of a halogen atom, a $C_1$–$C_4$ alkyl group, a $C_1$–$C_4$ alkoxy group, cyano, nitro, a heterocycle, an aryl group and an aryloxy group,
and X is a member selected from the group consisting of a halogen atom, —S—aryl, —S—heterocycle, and —PO$_3$R$_2$ wherein each R is independently selected from the group consisting of a hydrogen atom and $C_1$–$C_3$ alkyl;
$R^1$ and $R^2$ each independently represent a hydrogen atom, a lower alkyl group, an unsubstituted cycloalkyl group, a cycloalkyl group substituted with a lower alkyl or halogen, a group represented by the formula: —(CH$_2$)$_q$—A' wherein q is an integer of 1 to 4, and A' is a member selected from the group consisting of a hydroxyl group, a group represented by the formula:

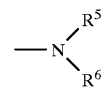

wherein $R^5$ and $R^6$ each independently represent a hydrogen atom, a lower alkyl group, or a group represented by the formula:

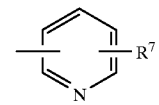

wherein $R^7$ represents a hydrogen atom, a lower alkyl group, or a group represented by the formula:

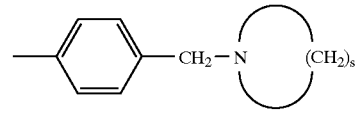

wherein s is an integer of 2 to 5, or
a cycloalkyl group condensed with an aromatic ring, a bicycloalkyl, or tricycloalkyl, said bicycloalkyl or tricycloalkyl being an aliphatic saturated hydrocarbon group made of two or three rings, respectively, with at least two carbon atoms being common to each ring, or an azabicycloalkyl group which is a bicycloalkyl group as described above in which one carbon atom is replaced by a nitrogen atom or a group represented by the formula:

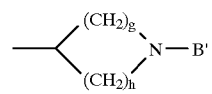

wherein g and h are each an integer of 1 to 4, and B' stands for a lower alkyl group, an arylalkyl group, an arylalkyl group substituted by lower alkyl, halogen or a lower alkoxy group, or a pyridylalkyl group, or a pyridylalkyl group substituted with a lower alkyl group, a halogen or a lower alkoxy group;
$R^3$ represents a hydrogen atom, a lower alkyl group, or a $C_3$–$C_8$ cycloalkyl group;
$R^4$ represents a hydrogen atom, a lower alkyl group, a lower alkoxy group or a halogen atom; wherein
n is an integer of 1 to 4, or, alternatively n, is 2, and the two $R^4$ groups may form a cyclohexenyl or phenyl ring together with two adjacent carbon atoms constituting the benzene ring;
wherein
an aryl group is a member selected from the group consisting of a phenyl ring and a naphthyl ring, wherein said aryl group is unsubstituted with at least one member selected from the group consisting of a halogen, an alkyl an alkoxy, an alkylthio, an trifluoromethyl, an acyloxy, a hydroxy, a mercapto, a carboxy, an aryloxy, an arylalkyl, a heteroaryl, a heterocycle and an amino group;
wherein
$C_3-C_8$ carbocycle is a member of the group consisting of a nonaromatic cyclic carbon compound having between 3 to 8 carbons in said ring and optionally having at least one site of unsaturation;
wherein
a heterocycle group is a member selected from the group consisting of a single ring or mutiple condensed rings, said heterocycle group having between four to ten total ring atoms wherein between one and four of said total ring atoms are heteroatoms selected from the group consisting of N, O, and S wherein said heterocycle group is optionally unsubstituted or substituted with at least one member selected from the group consisting of halogen, alkyl, cycloalkyl, alkoxy, alkylthio, trifluoromethyl, acyloxy, hydroxy, mercapto, carboxy aryloxy, aryl, arylalkyl, and heteroaryl; and any pharmacologically acceptable salts thereof.

22. A method in accordance with claim 21, wherein A is a radical of formula —CH=CH—B.

23. A method in accordance with claim 22, wherein B is alkyl, $R^3$ is methyl and $R^1$ is cycloheptyl.

24. A method in accordance with claim 22, wherein B is arylalkyl, $R^3$ is methyl and $R^1$ is cycloheptyl.

25. A method in accordance with claim 22, wherein B is a carbocycle, $R^3$ is methyl and $R^1$ is cycloheptyl.

26. A method in accordance with claim 22, wherein B is a heterocycle, $R^3$ is methyl and $R^1$ is cycloheptyl.

27. A method in accordance with claim 21, wherein A is aryl, $R^3$ is methyl and $R^1$ is cycloheptyl.

28. A method in accordance with claim 21, wherein A is alkyl, $R^3$ is methyl and $R^1$ is cycloheptyl.

29. A method in accordance with claim 21, wherein A is diphenylmethyl, $R^1$ is methyl and $R^1$ is cycloheptyl.

30. A method in accordance with claim 21, wherein A is phenoxyphenyl, $R^3$ is methyl and $R^1$ is cycloheptyl.

31. A method for the treatment of Alzheimer's disease in a patient, comprising administering to said patient an efficacious dose of a compound having the formula:

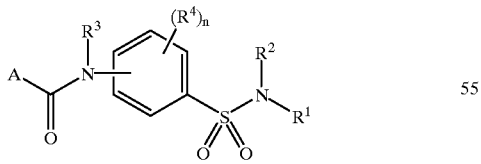

wherein
A represents a $C_4-C_{10}$ alkyl group, an aryl group, an arylalkyl group, radicals selected from the group consisting of —CH=CH—B, —S—B, and —NH—B, or radicals of formula —CH$_2$—X,
wherein B represents a non-aromatic $C_3-C_8$ carbocycle, a $C_3-C_8$ alkyl group, or a heterocycle, each of which is optionally substituted with one or more members independently selected from the group consisting of a halogen atom, a $C_1-C_4$ alkyl group, a $C_3-C_4$ alkoxy group, cyano, nitro, a heterocycle, an aryl group and an aryloxy group,
and X is a member selected from the group consisting of a halogen atom, —S—aryl, —S—heterocycle, and —PO$_3$R$_2$ wherein each R is independently selected from the group consisting of a hydrogen atom and $C_1-C_3$ alkyl;

$R^1$ and $R^2$ each independently represent a hydrogen atom, a lower alkyl group, an unsubstituted cycloalkyl group, a cycloalkyl group substituted with a lower alkyl or halogen, a group represented by the formula: —(CH$_2$)$_q$—A' wherein q is an integer of 1 to 4, and A' is a member selected from the group consisting of a hydroxyl group, a group represented by the formula:

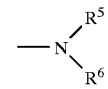

wherein $R^5$ and $R^6$ each independently represent a hydrogen atom, a lower alkyl group, or a group represented by the formula:

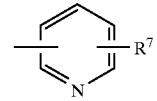

wherein $R^7$ represents a hydrogen atom, a lower alkyl group, or a group represented by the formula:

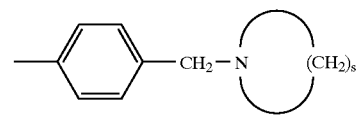

wherein s is an integer of 2 to 5, or
a cycloalkyl group condensed with an aromatic ring, a bicycloalkyl, or tricycloalkyl, said bicycloalkyl or tricycloalkyl being an aliphatic saturated hydrocarbon group made of two or three rings, respectively, with at least two carbon atoms being common to each ring, or an azabicycloalkyl group which is a bicycloalkyl group as described above in which one carbon atom is replaced by a nitrogen atom or a group represented by the formula:

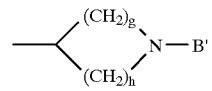

wherein g and h are each an integer of 1 to 4, and B' stands for a lower alkyl group, an arylalkyl group, an arylalkyl group substituted by lower alkyl, halogen or a lower alkoxy group, or a pyridylalkyl group, or a pyridylalkyl group substituted with a lower alkyl group, a halogen or a lower alkoxy group;

$R^3$ represents a hydrogen atom, a lower alkyl group, or a $C_3-C_8$ cycloalkyl group;

$R^4$ represents a hydrogen atom, a lower alkyl group, a lower alkoxy group or a halogen atom; wherein n is an integer of 1 to 4, or, alternatively, n is 2, and the two $R^4$ groups may form a cyclohexenyl or phenyl ring together with two adjacent carbon atoms constituting the benzene ring;

wherein an aryl group is a member selected from the group consisting of a phenyl ring and a naphthyl ring, wherein said aryl group is unsubstituted with at least one member selected from the group consisting of a halogen, an alkyl an alkoxy, an alkylthio, an trifluoromethyl, an acyloxy, a hydroxy, a mercapto, a carboxy, an aryloxy, an arylalkyl, a heteroaryl, a heterocycle and an amino group;

wherein $C_3$–$C_8$ carbocycle is a member of the group consisting of a nonaromatic cyclic carbon compound having between 3 to 8 carbons in said ring and optionally having at least one site of unsaturation;

wherein a heterocycle group is a selected from the group consisting of a single ring or mutiple condensed rings, said heterocycle group having between four to ten total ring atoms wherein between one and four of said total ring atoms are heteroatoms selected from the group consisting of N, O, and S wherein said heterocycle group is optionally unsubstituted or substituted with at least one member selected from the group consisting of halogen, alkyl, cycloalkyl alkoxy, alkylthio, trifluoromethyl, acyloxy, hydroxy, mercapto, carboxy aryloxy, aryl, arylakyl, and heteroaryl; and any pharmacologically acceptable salts thereof.

32. A method in accordance with claim 31, wherein A is a radical of formula —CH═CH—B.

33. A method in accordance with claim 32, wherein B is alkyl, $R^3$ is methyl and $R^1$ is cycloheptyl.

34. A method in accordance with claim 32, wherein B is arylalkyl, $R^3$ is methyl and $R^1$ is cycloheptyl.

35. A method in accordance with claim 32, wherein B is a carbocycle, $R^3$ is methyl and $R^1$ is cycloheptyl.

36. A method in accordance with claim 32, wherein B is a heterocycle, $R^3$ is methyl and $R^1$ is cycloheptyl.

37. A method in accordance with claim 31, wherein A is aryl, $R^3$ is methyl and $R^1$ is cycloheptyl.

38. A method in accordance with claim 31, wherein A is alkyl, $R^3$ is methyl and $R^1$ is cycloheptyl.

39. A method in accordance with claim 31, wherein A is diphenylmethyl, $R^3$ is methyl and $R^1$ is cycloheptyl.

40. A method in accordance with claim 31, wherein A is phenoxyphenyl, $R^3$ is methyl and $R^1$ is cycloheptyl.

* * * * *

UNITED STATES PATENT AND TRADEMARK OFFICE
CERTIFICATE OF CORRECTION

PATENT NO. : 5,994,398
DATED : November 30, 1999
INVENTOR(S) : John *et al.*

It is certified that error appears in the above-identified patent and that said Letters Patent is hereby corrected as shown below:

Claim 21, column 34, line 66, after "alternatively n", delete ",".
Claim 31, column 36, line 3, delete "$C_3$" and insert therefor --$C_1$--.
Claim 31, column 37, line 20, after "group is a" insert --member--.

Signed and Sealed this

Seventh Day of November, 2000

Attest:

Q. TODD DICKINSON

*Attesting Officer*          *Director of Patents and Trademarks*